US009920112B2

(12) United States Patent
Spector

(10) Patent No.: US 9,920,112 B2
(45) Date of Patent: *Mar. 20, 2018

(54) IMMUNOGLOBULIN-BINDING PROTEINS WITH IMPROVED SPECIFICITY

(71) Applicant: EMD Millipore Corporation, Burlington, MA (US)

(72) Inventor: Shari Spector, Lexington, MA (US)

(73) Assignee: EMD Millipore Corporation, Burlington, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 14/061,080

(22) Filed: Oct. 23, 2013

(65) Prior Publication Data

US 2014/0046037 A1  Feb. 13, 2014

Related U.S. Application Data

(63) Continuation of application No. 12/462,484, filed on Aug. 4, 2009, now Pat. No. 8,592,555.

(60) Provisional application No. 61/212,812, filed on Apr. 16, 2009, provisional application No. 61/188,549, filed on Aug. 11, 2008.

(51) Int. Cl.
| C07K 16/12 | (2006.01) |
| C07K 1/22 | (2006.01) |
| C07K 14/31 | (2006.01) |
| B01J 20/286 | (2006.01) |
| B01J 20/32 | (2006.01) |

(52) U.S. Cl.
CPC ......... *C07K 16/1271* (2013.01); *B01J 20/286* (2013.01); *B01J 20/3274* (2013.01); *C07K 1/22* (2013.01); *C07K 14/31* (2013.01)

(58) Field of Classification Search
None
See application file for complete search history.

(56) References Cited

U.S. PATENT DOCUMENTS

| 4,617,266 A | 10/1986 | Fahnestock |
| 4,879,378 A | 11/1989 | Foster et al. |
| 5,084,559 A | 1/1992 | Profy |
| 5,143,844 A | 9/1992 | Abrahmsen et al. |
| 5,151,350 A | 9/1992 | Colbert et al. |
| 5,198,531 A | 3/1993 | Webber et al. |
| 5,240,680 A | 8/1993 | Zuckermann et al. |
| 5,260,373 A | 11/1993 | Profy et al. |
| 5,580,757 A | 12/1996 | Desnick et al. |
| 6,013,763 A | 1/2000 | Braisted et al. |
| 6,060,596 A | 5/2000 | Lerner et al. |
| 6,197,927 B1 | 3/2001 | Braisted et al. |
| 6,399,750 B1 | 6/2002 | Johansson |
| 6,602,977 B1 | 8/2003 | Ljungqvist et al. |
| 6,831,161 B1 | 12/2004 | Uhlen et al. |
| 7,026,446 B1 | 4/2006 | Atwell et al. |
| 7,083,948 B1 | 8/2006 | Sassenfeld et al. |
| 7,163,686 B1 | 1/2007 | Silverman |
| 7,192,738 B2 | 3/2007 | Lowman et al. |
| 7,311,918 B2 | 12/2007 | Choi et al. |
| 7,691,608 B2 | 4/2010 | Peyser |
| 7,709,209 B2 | 5/2010 | Hober et al. |
| 7,833,723 B2 | 11/2010 | Bian et al. |
| 7,834,158 B2 | 11/2010 | Hober |
| 7,846,682 B2 | 12/2010 | Bian et al. |
| 7,847,071 B2 | 12/2010 | Bonnerjea et al. |
| 8,329,860 B2 | 12/2012 | Hall et al. |
| 8,754,196 B2 | 6/2014 | Spector et al. |
| 2003/0059910 A1 | 3/2003 | Moloney et al. |
| 2005/0100970 A1 | 5/2005 | Uhlen et al. |
| 2005/0171339 A1 | 8/2005 | Sugo et al. |
| 2006/0030696 A1 | 2/2006 | Bonnerjea et al. |
| 2006/0134805 A1 | 6/2006 | Berg et al. |
| 2006/0194950 A1 | 8/2006 | Hober et al. |
| 2006/0194955 A1 | 8/2006 | Hober et al. |
| 2006/0205016 A1* | 9/2006 | Silverman ............... C07K 14/31 435/7.1 |
| 2007/0207500 A1 | 9/2007 | Bian et al. |
| 2008/0096819 A1 | 4/2008 | Grabstein et al. |
| 2008/0108053 A1 | 5/2008 | Patchornik |
| 2008/0210615 A1 | 9/2008 | Joehnck et al. |
| 2008/0255027 A1 | 10/2008 | Moya et al. |
| 2009/0246885 A1 | 10/2009 | Bian et al. |
| 2009/0299035 A1 | 12/2009 | Iwakura et al. |
| 2009/0317381 A1 | 12/2009 | Plaut et al. |
| 2010/0022760 A1 | 1/2010 | Hober et al. |
| 2010/0048876 A1 | 2/2010 | Hall et al. |

(Continued)

FOREIGN PATENT DOCUMENTS

| CN | 1642976 A | 7/2005 |
| CN | 101522278 A | 9/2009 |

(Continued)

OTHER PUBLICATIONS

Notice of Opposition received in European Patent Application No. 09180615.8 on Dec. 19, 2013, 24 pages.
Amersham Biosciences, "rmp Protein A Sepharose Fast Flow", Data File, Affinity Chromatography, 2000, pp. 1-4.
Chen et al., "Immobilized Protein ZZ, an Affinity Tool for Immunoglobulin Isolation and Immunological Experimentation", Biotechnology and Applied Biochemistry, vol. 45, 2006, pp. 87-92.
Gronberg et al., "Rapid Development of CIP Protocols for Affinity Media", Poster Presented at the SPICA Conference, Zurich, Sep. 29-Oct. 1, 2008, 1 page.
Pall Life Sciences, "Protein A Ceramic HyperD F-Affinity Chromatography Sorbent", Product Note LPN PN702-004, Dec. 2004, pp. 1-6.

(Continued)

Primary Examiner — Daniel E Kolker
Assistant Examiner — James Rogers
(74) Attorney, Agent, or Firm — EMD Millipore Corporation

(57) ABSTRACT

The present invention relates to modified immunoglobulin-binding proteins, e.g., *Staphylococcus* protein A, having improved binding specificity for immunoglobulins and methods of making and using the same.

8 Claims, 24 Drawing Sheets

(56) References Cited

U.S. PATENT DOCUMENTS

| | | | |
|---|---|---|---|
| 2010/0063256 A1 | 3/2010 | Spector | |
| 2010/0130721 A1 | 5/2010 | Iwakura et al. | |
| 2010/0168395 A1 | 7/2010 | Sato | |
| 2010/0221844 A1* | 9/2010 | Bian | B01D 15/3809 |
| | | | 436/501 |
| 2010/0286373 A1 | 11/2010 | Majima et al. | |
| 2012/0208234 A1 | 8/2012 | Yoshida et al. | |

FOREIGN PATENT DOCUMENTS

| | | |
|---|---|---|
| CN | 101704879 A | 5/2010 |
| CN | 101775069 A | 7/2010 |
| EP | 0230869 A2 | 8/1987 |
| EP | 0550771 A1 | 7/1993 |
| EP | 1564286 A1 | 8/2005 |
| EP | 1123389 B1 | 10/2005 |
| EP | 1601697 B1 | 5/2007 |
| EP | 1972689 A2 | 9/2008 |
| EP | 1992692 A1 | 11/2008 |
| EP | 2014359 A1 | 1/2009 |
| EP | 2066419 A1 | 6/2009 |
| EP | 2157099 A1 | 2/2010 |
| EP | 2202310 A2 | 6/2010 |
| JP | 2005-538693 A | 12/2005 |
| JP | 2006-304633 A | 11/2006 |
| JP | 2007-525412 A | 9/2007 |
| JP | 2007-537700 A | 12/2007 |
| JP | 2008-255046 A | 10/2008 |
| JP | 5480558 B2 | 4/2014 |
| RU | 2415865 C2 | 4/2011 |
| WO | 1984/000773 A1 | 3/1984 |
| WO | 1990/002182 A1 | 3/1990 |
| WO | 1990/009237 A1 | 8/1990 |
| WO | 1995/019374 A1 | 7/1995 |
| WO | 1997/017361 A1 | 5/1997 |
| WO | 1997/036614 A1 | 10/1997 |
| WO | 2000/023580 A1 | 4/2000 |
| WO | 2000/063243 A1 | 10/2000 |
| WO | 2000/069457 A1 | 11/2000 |
| WO | 2003/080655 A1 | 10/2003 |
| WO | 2004/076485 A1 | 9/2004 |
| WO | 2005/003156 A1 | 1/2005 |
| WO | 2006004067 A1 | 1/2006 |
| WO | 2006/070416 A1 | 7/2006 |
| WO | 2006/092338 A2 | 9/2006 |
| WO | 2007/019376 A2 | 2/2007 |
| WO | 2007/138328 A2 | 12/2007 |
| WO | 2008/039141 A1 | 4/2008 |
| WO | 2008/091740 A2 | 7/2008 |
| WO | 2008/127457 A2 | 10/2008 |
| WO | 2009/138484 A2 | 11/2009 |
| WO | 2009/146755 A1 | 12/2009 |
| WO | 2010/080065 A1 | 7/2010 |
| WO | 2010/110288 A1 | 9/2010 |
| WO | 2012/074463 A1 | 6/2012 |

OTHER PUBLICATIONS

Extended European Search Report received for EP Patent Application No. 09167670.0, dated Dec. 30, 2009, 7 pages.
Extended European Search Report received for EP Patent Application No. 09180615.8, dated Sep. 16, 2010, 18 pages.
Partial European Search Report received for EP Patent Application No. 09180615.8, dated May 20, 2010, 8 pages.
Altschul et al., "Basic Local Alignment Search Tool", Journal of Molecular Biology, vol. 215, 1990, pp. 403-410.
Arshady, Reza, "Styrene Based Polymer Supports Developed by Suspension Polymerization", Chimica e L'Industria, vol. 70, No. 9, 1988, pp. 70-75.
Bowie et al., "Deciphering the Message in Protein Sequences: Tolerance to Amino Acid Substitutions", Science, vol. 247, Mar. 16, 1990, pp. 1306-1310.
Boyle et al., "Bacterial Fc Receptors", Nature Biotechnology, vol. 5, 1987, pp. 697-703.
Flatmark et al., "Multiple Forms of Cytochrome c in the Rat. Precursor-product Relationship between the Main Component Cy I and the Minor Components Cy II and Cy 3 in Vivo", The Journal of Biological Chemistry, vol. 243, No. 7, Apr. 10, 1968, pp. 1623-1629.
Flatmark, T.,"On the Heterogeneity of Beef Heart Cytochrome c", Acta Chemica Scandinavica, vol. 18, 1964, pp. 1656-1666.
Ghose et al., "Antibody Variable Region Interactions with Protein A: Implications for the Development of Generic Purification Processes", Biotechnology and Bioengineering, vol. 92, No. 6, Dec. 20, 2005, pp. 665-673.
Ghose et al., "Protein A Affinity Chromatography for Capture and Purification of Monoclonal Antibodies and Fc-Fusion Proteins: Practical Considerations for Process Development", Chapter 16: Process Scale Bioseparations for the Biopharmaceutical Industry, edited by Shukla et al. CRC Press, 2007, pp. 463-489.
Graille et al., "Crystal structure of a *Staphylococcus aureus* Protein A Domain Complexed with the Fab Fragment of a Human IgM Antibody: Structural basis for Recognition of B-cell Receptors and Superantigen Activity", Proceedings of the National Academy of Sciences, vol. 97, No. 10, May 9, 2000, 5399-5404.
Gulich et al., "Protein Engineering of an IgG-binding Domain Allows Milder Elution Conditions During Affinity Chromatography", Journal of Biotechnology, vol. 76, No. 2-3, Jan. 21, 2000, pp. 233-243.
Henikoff et al., "Amino acid Substitution Matrices from Protein Blocks", Proceedings of the National Academy of Sciences, vol. 89, Nov. 1992, pp. 10915-10919.
Hermanson et al., "Activation Methods", Chapter 2, Affinity Ligand Techniques, Academic Press, 1992, pp. 51-136.
Hjerten, Stellan, "The Preparation of Agarose Spheres for Chromatography of Molecules and Particles", Biochimica et Biophysica Acta, vol. 79, No. 2, Mar. 30, 1964, pp. 393-398.
Hober et al., "Protein A Chromatography for Antibody Purification", Journal of Chromatography B, vol. 848, No. 1, Mar. 15, 2007, pp. 40-47.
Hulett et al., "The Second and Third Extracellular Domains of FcγRI (CD64) Confer the Unique High Affinity Binding of IgG2a", Molecular Immunology, vol. 35, 1998, pp. 989-996.
Huston et al., "Multisite Association by Recombinant Proteins can Enhance Binding Selectivity", Biophysical Journal, vol. 62, 1992, pp. 87-91.
Jansson et al., "All Individual Domains of Staphylococcal Protein A Show Fab Binding", FEMS Immunology & Medical Microbiology, vol. 20, No. 1, Jan. 1998, pp. 69-78.
Ljungberg et al., "The Interaction between Different Domains of Staphylococcal Protein A and Human Polyclonal IgG, IgA, IgM and F(ab')2: Separation of Affinity from Specificity", Molecular Immunology, vol. 30, No. 14, Oct. 1993, pp. 1279-1285.
Ljungquist et al., "Thiol-Directed Immobilization of Recombinant IgG-binding Receptors", European Journal of Biochemistry, vol. 186, No. 3, Dec. 22, 1989, pp. 557-561.
McKerrow et al., "Deamidation of Asparaginyl Residues as a Hazard in Experimental Protein and Peptide Procedures", Anal. Biochem., vol. 42, No. 2, Aug. 1971, pp. 565-568.
McKerrow et al., "Primary Sequence Dependence of the Deamidation of Rabbit Muscle Aldolase", Science, vol. 183. No. 4120, Jan. 11, 1974, p. 85.
Needleman et al., "A General Method Applicable to the Search for Similarities in the Amino Acid Sequence of Two Proteins", Journal of molecular biology, vol. 48, 1970, pp. 443-453.
Nilsson et al., "A synthetic IgG-binding Domain based on Staphylococcal Protein A", Protein Engineering, vol. 1, No. 2, 1987, pp. 107-113.
Pearson et al., "Improved Tools for Biological Sequence Comparison", Proceedings of the National Academy of Sciences, vol. 85, No. 8, Apr. 1, 1988, pp. 2444-2448.
Porath et al., "Group Fractionation of Plasma Proteins on Dipolar Ion Exchangers", Journal of Chromatography A, vol. 51, 1970, pp. 479-489.

(56) References Cited

OTHER PUBLICATIONS

Robinson et al., "Controlled Deamidation of Peptides and Proteins: An Experimental Hazard and a Possible Biological Timer", Proceedings of the National Academy of Sciences, vol. 66, No. 3, Jul. 1970, pp. 753-757.
Robinson et al., "Rates of Nonenzymatic Deamidation of Glutaminyl and Asparaginyl Residues in Pentapeptides", Journal of the American Chemical Society, vol. 95, No. 24, Nov. 28, 1973, pp. 8156-8159.
Robinson et al., "Sequence Dependent Deamidation Rates for Model Peptides of Cytochrome C", Int. J. Peptide Protein Res., vol. 6, No. 1, 1974, pp. 31-35.
Robinson et al., "Sequence Dependent Deamidation Rates for Model Peptides of Histone IV", Int. J. Peptide Protein Res., vol. 6, No. 5, 1974, pp. 279-282.
Scotchler et al., "Deamidation of Glutaminyl Residues: Dependence on pH, Temperature, and Ionic Strength", Analytical Biochemistry, vol. 59, No. 1, May 1974, pp. 319-322.
Sjodahl et al., "Structural Studies on the Four Repetitive Fc-Binding Regions in Protein A from *Staphylococcus aureus*", European Journal of Biochemistry, vol. 78, No. 2, Sep. 1977, pp. 471-490.
Smith et al., "Comparison of Biosequences", Advances in Applied Mathematics, vol. 2, No. 4, Dec. 1981, pp. 482-489.
Starovasnik et al., "Antibody Variable Region Binding by Staphylococcal Protein A: Thermodynamic Analysis and Location of the Fv Binding Site on E-domain", Protein Science, vol. 8, No. 7, Jul. 1999, pp. 1423-1431.
Murray et al., "Harper's Biochemistry", 23rd Edition, Chapter 4, Section I, "Structure and Functions of Proteins and Enzymes", Amino Acids, 1993, pp. 23-28.
Uhlen et al., "Complete Sequence of the Staphylococcal Gene Encoding Protein A:A Gene Evolved Through Multiple Duplications", The Journal of Biological Chemistry, vol. 259, No. 3, Feb. 10, 1984, pp. 1695-1702.
"Affinity Chromatography—Principles and Methods", GE Healthcare, Oct. 2007, pp. 28-37.
Observation filed for the European application No. 09180615.8, Jun. 3, 2014, 17 pages.
"MabSelect SuRe—Studies on Ligand Toxicity, Leakage, Removal of Leached Ligand, and Sanitization", 11-0011-64 AA, Nov. 2004, Amersham Application Note, Process-scale Antibody Purification, Amersham Biosciences, 2004, pp. 1-6.
Extended European Search Report and European Search Opinion received for European Patent Application No. 12163614.6, dated Aug. 8, 2012, 8 pages.
Extended European Search Report and European Search Opinion received for European Patent Application No. 12163615.3, dated Aug. 8, 2012, 8 pages.
Extended European Search Report and European Search Opinion received for European Patent Application No. 12171108.9, dated Oct. 2, 2012, 16 pages.
Braisted et al., "Minimizing a Binding Domain from Protein A", Proc. Natl. Acad. Sci. USA, vol. 93, Jun. 1996, pp. 5688-5692.
Brown et al., "A Study of the Interactions Between an IgG-Binding Domain Based on the B Domain of Staphylococcal Protein A and Rabbit IgG", Molecular Biotechnology, vol. 10, 1998, pp. 9-16.
Brown et al., "Affinity Purification of Human IgG using Immobilised, Mutated Immunoglobulin-Binding Domains from Protein A of *Staphylococcus aureus*", Biochemical Society Transactions, vol. 26, 1998, p. S249.
Cedergren et al., "Mutational Analysis of the Interaction between Staphylococcal Protein A and Human IgG", Protein Engineering, vol. 6, No. 4, 1993, pp. 441-448.
Deisenhofer, Johann, "Crystallographic Refinement and Atomic Models of a Human Fc Fragment and its Complex with Fragment B of Protein A From *Staphylococcus aureus* at 2.9- and 2.8-Å Resolution", Biochemistry, vol. 20, No. 9, Apr. 28, 1981, pp. 2361-2370.
Füglistaller, Paul, "Comparison of Immunogloublin Binding Capacities and Ligand Leakage Using Eight Different Protein A Affinity Chromatography Matrices", Journal of Immunological Methods, vol. 124, 1989, pp. 171-177.
Geiger et al., "Deamidation, Isomerization, and Racemization at Asparaginyl and Aspartyl Residues in Peptides", The Journal of Biological Chemistry, vol. 262, No. 2, Jan. 15, 1987, pp. 785-794.
Godfrey et al., "A Sensitive Enzyme-Linked Immunosorbent Assay (ELISA) for the Detection of Staphylococcal Protein A (SpA) Present as a Trace Contaminant of Murine Immunoglobulins Purified on Immobilized Protein A", Journal of Immunological Methods, vol. 149, 1992, pp. 21-27.
Hale et al., "Repeated Cleaning of Protein A Affinity Column with Sodium Hydroxide", Journal of Immunological Methods, vol. 171, 1994, pp. 15-21.
Linhult et al., "Mutational Analysis of the Interaction between Albumin-Binding Domain from Streptococcal Protein G and Human Serum Albumin", Protein Science, vol. 11, 2002, pp. 206-213.
Nord et al., "Binding Proteins Selected from Combinatorial Libraries of an α-Helical Bacterial Receptor Domain", Nature Biotechnology, vol. 15, Aug. 1997, pp. 772-777.
O'Cuinn, G., "Peptide Metabolism in Cytoplasm of Brain Cell", Biochemical Society Transactions, vol. 26, No. 3, 1998, pp. 279-292.
Pace et al., "How to Measure and Predict the Molar Absorption Coefficient of a Protein", Protein Science, vol. 4, 1995, pp. 2411-2423.
Patel et al., "Chemical Pathways of Peptide Degradation. II. Kinetics of Deamidation of an Asparaginyl Residue in a Model Hexapeptide", Pharmaceutical Research, vol. 7, No. 7, 1990, pp. 703-711.
Popplewell et al., "Synthesis and Mutagenesis of an IgG-Binding Protein based upon Protein A of *Staphylococcus aureus*", Protein Engineering, vol. 4, No. 8, 1991, pp. 963-970.
Saito et al., "High Level Expression of a Synthetic Gene Coding for IgG-Binding Domain B of Staphylococcal Protein A", Protein Engineering, vol. 2, No. 6, 1989, pp. 481-487.
Partial European Search Report received for EP Patent Application No. 12171045.3, dated Sep. 24, 2012, 8 pages.
Extended European Search Report and Search Opinion received for EP Patent Application No. 12171045.3, dated Mar. 5, 2013, 19 pages.
International Search Report received for PCT Patent Application No. PCT/US2012/041070, dated Aug. 14, 2013, 7 pages.
Atkins et al., "*S. aureus* IgG-Binding Proteins SpA and Sbi: Host Specificity and Mechanisms of Immune Complex Formation", Molecular Immunology, vol. 45, 2008, pp. 1600-1611.
Palmer et al., "Design of Stability at Extreme Alkaline pH in Streptococcal Protein G", Journal of Biotechnology, vol. 134, 2008, pp. 222-230.
Roque et al., "Affinity-Based Methodologies and Ligands for Antibody Purification: Advances and Perspectives", Journal of Chromatography A, vol. 1160, 2007, pp. 44-55.
"UniProt Database Accession No. Q683L6", available online at <http://www.uniprot.org/uniprot/Q683L6.txt>, retrieved on May 3, 2013, 1 page.
"UniProt Database Accession No. H3Z2S0", available online at <http://www.uniprot.org/uniprot/H3Z2S0.txt>, retrieved on May 3, 2013, 1 page.
"UniProt Database Accession No. H3YRJ6", available online at <http://www.uniprot.org/uniprot/H3YRJ6.txt>, retrieved on May 3, 2013, 1 page.
Unpublished Japanese Patent Application No. 2009-71766, filed on Mar. 24, 2009, Yoshida et al., titled "Protein having Affinity for Immunoglobulin, and Immunoglobulin-Binding Affinity Ligand " (Corresponds to U.S 20120208234 A1).
Extended European Search Report and European Search Opinion received for European Patent Application No. 14163423.8, dated Oct. 7, 2014, 10 pages.
International Preliminary Report on Patentability received for PCT Patent Application No. PCT/US2012/041070, dated Dec. 27, 2013, 13 pages.

(56) References Cited

OTHER PUBLICATIONS

Geneseq "*S. aureus* SpA Protein Inmunoglobul in-Binding Domain SpA-C.", Retrieved from EBI Accession No. GSP: AOD36812, Apr. 17, 2008, 2 pages.
Database WPI, "Week 200702", Thomson Scientific, London, GB, AN 2007-012290, XP002683879, retrieved on Sep. 26, 2012, 2 pages.

* cited by examiner

DNA Sequences of the wt IgG binding domains of Protein A

SEQ ID NO:1- E domain DNA sequence
GCGCAACAAAACGCTTTCTATCAGGTACTGAACATGCCTAACCTGAACGCCGATCAGCG
TAACGGCTTCATCCAAAGCCTGAAGGACGACCCGAGCCAGTCCGCAAACGTTCTGGGTG
AAGCTCAAAAACTGAACGACAGCCAGGCACCGAAAGCTGAC SEQ ID NO:2- D domain DNA sequence
GCCCAACAGAACAAATTTAACAAAGACCAGCAGTCCGCGTTCTACGAGATTCTGAACAT
GCCTAACCTGAATGAAGAACAGCGCAACGGTTTTATTCAGTCTCTGAAGGACGATCCTT
CTCAATCCACCAACGTACTGGGCGAAGCGAAGAAACTGAACGAATCTCAGGCTCCGAAG SEQ ID NO:3- A domain DNA sequence
GCCGACAACAACTTCAACAAAGAGCAGCAAAACGCTTTCTACGAAATCCTGAATATGCC
AAATCTGAACGAAGAGCAGCGTAACGGTTTCATCCAATCTCTGAAAGACGATCCGTCCC
AGTCCGCGAATCTGCTGGCGGAGGCTAAAAAGCTGAACGAATCCCAGGCTCCGAAA SEQ ID NO:4- B domain DNA sequence
GCAGACAATAAGTTCAATAAAGAGCAGCAGAACGCATTTTACGAGATCCTGCATCTGCC
GAACCTGAACGAAGAACAACGCAACGGTTTCATTCAGAGCCTGAAAGACGACCCATCTC
AGTCCGCTAACCTGCTGGCGGAAGCAAAGAAGCTGAACGATGCACAGGCGCCGAAA SEQ ID NO:5- C domain DNA sequence
GCGGATAACAAATTCAACAAGGAGCAACAGAACGCATTCTATGAAATTCTGCACCTGCC
GAATCTGACGGAGGAGCAACGTAACGGCTTTATCCAGTCCCTGAAGGATGATCCGTCTG
TGTCTAAAGAGATCCTGGCGGAGGCAAAAAAACTGAATGATGCACAAGCTCCGAAA

Figure 1

SEQ ID NO:6- Z domain DNA sequence
GTAGACAACAAATTCAATAAAGAACAGCAGAACGCTTTCTATGAAATCCTGCACCTGCC
GAACCTGAACGAAGAACAGCGTAACGCGTTTATCCAGTCCCTGAAAGACGACCCGAGCC
AGAGCGCAAATCTGCTGGCGGAAGCGAAAAAGCTGAACGATGCCCAGGCGCCGAAA

Figure 2

IgG binding domain sequence alignment

```
E   ----------AQQNAFYQVLNMPNLNADQRNGFIQSLKDDPSQSANVLGEAQKLNDSQAPK 51  (SEQ ID NO:7)
D   ADAQQNKFNKDQQSAFYEILNMPNLNEEQRNGFIQSLKDDPSQSTNVLGEAKKLNESQAPK 61  (SEQ ID NO:8)
A   --ADNR-FNKEQQNAFYEILNMPNLNEEQRNGFIQSLKDDPSQSANLLAEAKKLNESQAPK 58  (SEQ ID NO:9)
B   ---ADNKFNKEQQNAFYEILHLPNLNEEQRNGFIQSLKDDPSQSANLLAEAKKLNDAQAPK 58  (SEQ ID NO:10)
C   ---ADNKFNKEQQNAFYEILHLPNLTEEQRNGFIQSLKDDPSVSKEILAEAKKLNDAQAPK 58  (SEQ ID NO:11)
             ** ****.:; *****  **:***********.* ;:*,.******;:****
```

Figure 3

SEQ ID NO:12- Z domain amino acid sequence
VDNKFNKEQQ NAFYEILHLP NLNEEQRNAF IQSLKDDPSQ SANLLAEAKKL
NDAQAPK

Figure 4

B domain variant DNA sequences

SEQ ID NO: 14- G29K
GCAGACAATAAGTTCAATAAAGAGCAGCAGAACGCATTTTACGAGATCCTGCATCTGCC
GAACCTGAACGAAGAACAACGCAACAAATTCATTCAGAGCCTGAAAGACGACCCATCTC
AGTCCGCTAACCTGCTGGCGGAAGCAAAGAAGCTGAACGATGCACAGGCGCCGAAA

SEQ ID NO: 13- G29L
GCAGACAATAAGTTCAATAAAGAGCAGCAGAACGCATTTTACGAGATCCTGCATCTGCC
GAACCTGAACGAAGAACAACGCAACCGCTTCATTCAGAGCCTGAAAGACGACCCATCTC
AGTCCGCTAACCTGCTGGCGGAAGCAAAGAAGCTGAACGATGCACAGGCGCCGAAA

SEQ ID NO:15- G29R
GCAGACAATAAGTTCAATAAAGAGCAGCAGAACGCATTTTACGAGATCCTGCATCTGCC
GAACCTGAACGAAGAACAACGCAACCTGTTCATTCAGAGCCTGAAAGACGACCCATCTC
AGTCCGCTAACCTGCTGGCGGAAGCAAAGAAGCTGAACGATGCACAGGCGCCGAAA

Figure 6

B domain variant amino acid sequences

SEQ ID NO:17- G29K
ADNKFNKEQQ NAFYEILHLP NLNEEQRNKF IQSLKDDPSQ SANLLAEAKKL
NDAQAPK

SEQ ID NO:16- G29L
ADNKFNKEQQ NAFYEILHLP NLNEEQRNLF IQSLKDDPSQ SANLLAEAKKL
NDAQAPK

SEQ ID NO:18- G29R
ADNKFNKEQQ NAFYEILHLP NLNEEQRNRF IQSLKDDPSQ SANLLAEAKKL
NDAQAPK

SEQUENCE LISTING

<160> NUMBER OF SEQ ID NOS: 31

<210> SEQ ID NO 1
<211> LENGTH: 159
<212> TYPE: DNA
<213> ORGANISM: Staphylococcus aureus

<400> SEQUENCE: 1
gcgcaacaaa acgctttcta tcaggtactg aacatgccta acctgaacgc cgatcagcgt    60
aacggcttca tccaaagcct gaaggacgac ccgagccagt ccgcaaacgt tctgggtgaa   120
gctcaaaaac tgaacgacag ccaggcaccg aaagctgac                          159

<210> SEQ ID NO 2
<211> LENGTH: 177
<212> TYPE: DNA
<213> ORGANISM: Staphylococcus aureus

<400> SEQUENCE: 2
gcccaacaga acaaatttaa caaagaccag cagtccgcgt tctacgagat tctgaacatg    60
cctaacctga atgaagaaca gcgcaacggt tttattcagt ctctgaagga cgatccttct   120
caatccacca acgtactggg cgaagcgaag aaactgaacg aatctcaggc tccgaag      177

<210> SEQ ID NO 3
<211> LENGTH: 174
<212> TYPE: DNA
<213> ORGANISM: Staphylococcus aureus

<400> SEQUENCE: 3
gccgacaaca acttcaacaa agagcagcaa aacgctttct acgaaatcct gaatatgcca    60
aatctgaacg aagagcagcg taacggtttc atccaatctc tgaaagacga tccgtcccag   120
tccgcgaatc tgctggcgga ggctaaaaag ctgaacgaat cccaggctcc gaaa         174

<210> SEQ ID NO 4
<211> LENGTH: 174
<212> TYPE: DNA
<213> ORGANISM: Staphylococcus aureus

<400> SEQUENCE: 4
gcagacaata agttcaataa agagcagcag aacgcatttt acgagatcct gcatctgccg    60
aacctgaacg aagaacaacg caacggtttc attcagagcc tgaaagacga cccatctcag   120
tccgctaacc tgctggcgga agcaaagaag ctgaacgatg cacaggcgcc gaaa         174

<210> SEQ ID NO 5
<211> LENGTH: 174
<212> TYPE: DNA
<213> ORGANISM: Staphylococcus aureus

<400> SEQUENCE: 5
gcggataaca aattcaacaa ggagcaacag aacgcattct atgaaattct gcacctgccg    60
aatctgacgg aggagcaacg taacggcttt atccagtccc tgaaggatga tccgtctgtg   120
tctaaagaga tcctggcgga ggcaaaaaaa ctgaatgatg cacaagctcc gaaa         174

<210> SEQ ID NO 6
<211> LENGTH: 174
<212> TYPE: DNA
<213> ORGANISM: Staphylococcus aureus

<400> SEQUENCE: 6

```
gtagacaaca aattcaataa agaacagcag aacgctttct atgaaatcct gcacctgccg      60
aacctgaacg aagaacagcg taacgcgttt atccagtccc tgaaagacga cccgagccag    120
agcgcaaatc tgctggcgga agcgaaaaag ctgaacgatg cccaggcgcc gaaa          174
```

<210> SEQ ID NO 7
<211> LENGTH: 51
<212> TYPE: PRT
<213> ORGANISM: Staphylococcus aureus

<400> SEQUENCE: 7

Ala Gln Gln Asn Ala Phe Tyr Gln Val Leu Asn Met Pro Asn Leu Asn
1               5                   10                  15

Ala Asp Gln Arg Asn Gly Phe Ile Gln Ser Leu Lys Asp Asp Pro Ser
            20                  25                  30

Gln Ser Ala Asn Val Leu Gly Glu Ala Gln Lys Leu Asn Asp Ser Gln
        35                  40                  45

Ala Pro Lys
    50

<210> SEQ ID NO 8
<211> LENGTH: 61
<212> TYPE: PRT
<213> ORGANISM: Staphylococcus aureus

<400> SEQUENCE: 8

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 9
<211> LENGTH: 58
<212> TYPE: PRT
<213> ORGANISM: Staphylococcus aureus

<400> SEQUENCE: 9

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 10
<211> LENGTH: 58
<212> TYPE: PRT
<213> ORGANISM: Staphylococcus aureus

<400> SEQUENCE: 10

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln

```
                    20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 11
<211> LENGTH: 58
<212> TYPE: PRT
<213> ORGANISM: Staphylococcus aureus

<400> SEQUENCE: 11

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
        50                  55

<210> SEQ ID NO 12
<211> LENGTH: 58
<212> TYPE: PRT
<213> ORGANISM: Staphylococcus aureus

<400> SEQUENCE: 12

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 13
<211> LENGTH: 174
<212> TYPE: DNA
<213> ORGANISM: Staphylococcus aureus

<400> SEQUENCE: 13
gcagacaata agttcaataa agagcagcag aacgcatttt acgagatcct gcatctgccg      60
aacctgaacg aagaacaacg caaccgcttc attcagagcc tgaaagacga cccatctcag     120
tccgctaacc tgctggcgga agcaaagaag ctgaacgatg cacaggcgcc gaaa           174

<210> SEQ ID NO 14
<211> LENGTH: 174
<212> TYPE: DNA
<213> ORGANISM: Staphylococcus aureus

<400> SEQUENCE: 14
gcagacaata agttcaataa agagcagcag aacgcatttt acgagatcct gcatctgccg      60
aacctgaacg aagaacaacg caacaaattc attcagagcc tgaaagacga cccatctcag     120
tccgctaacc tgctggcgga agcaaagaag ctgaacgatg cacaggcgcc gaaa           174

<210> SEQ ID NO 15
<211> LENGTH: 174
```

<212> TYPE: DNA
<213> ORGANISM: Staphylococcus aureus

<400> SEQUENCE: 15
gcagacaata agttcaataa agagcagcag aacgcatttt acgagatcct gcatctgccg      60
aacctgaacg aagaacaacg caacctgttc attcagagcc tgaaagacga cccatctcag     120
tccgctaacc tgctggcgga agcaaagaag ctgaacgatg cacaggcgcc gaaa           174

<210> SEQ ID NO 16
<211> LENGTH: 58
<212> TYPE: PRT
<213> ORGANISM: Staphylococcus aureus

<400> SEQUENCE: 16

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Leu Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 17
<211> LENGTH: 58
<212> TYPE: PRT
<213> ORGANISM: Staphylococcus aureus

<400> SEQUENCE: 17

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Staphylococcus aureus

<400> SEQUENCE: 18

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Arg Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer -continued

```
<220> FEATURE:
<221> NAME/KEY: modified_base
<222> LOCATION: (16)..(18)
<223> OTHER INFORMATION: a, c, t, g, unknown or other

<400> SEQUENCE: 19
gaagaacaac gcaacnnntt cattcaga                                              28

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttcaggttc ggcagatgca ggat                                                  24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaatatggct cataacaccc cttg                                                  24

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 22

His His His His His His
1               5

<210> SEQ ID NO 23
<211> LENGTH: 58
<212> TYPE: PRT
<213> ORGANISM: Staphylococcus aureus

<400> SEQUENCE: 23

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 24
<211> LENGTH: 58
<212> TYPE: PRT
<213> ORGANISM: Staphylococcus aureus

<400> SEQUENCE: 24

Ala Asp Asn Lys Phe Asn Lys Glu Gln Gln Asn Ala Phe Tyr Glu Ile
1               5                   10                  15
```

```
Leu His Leu Pro Asn Leu Asn Glu Glu Gln Arg Asn Leu Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 25
<211> LENGTH: 58
<212> TYPE: PRT
<213> ORGANISM: Staphylococcus aureus

<400> SEQUENCE: 25

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Arg Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 26
<211> LENGTH: 58
<212> TYPE: PRT
<213> ORGANISM: Staphylococcus aureus

<400> SEQUENCE: 26

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 27
<211> LENGTH: 58
<212> TYPE: PRT
<213> ORGANISM: Staphylococcus aureus

<400> SEQUENCE: 27

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Leu Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 28
<211> LENGTH: 58
<212> TYPE: PRT
<213> ORGANISM: Staphylococcus aureus

<400> SEQUENCE: 28

```
Ala Asp Asn Lys Phe Asn Lys Glu Gln Gln Asn Ala Phe Tyr Glu Ile
```

```
                1               5                       10                      15
Leu His Leu Pro Asn Leu Thr Glu Glu Gln Arg Asn Arg Phe Ile Gln
                20                      25                      30

Ser Leu Lys Asp Asp Pro Ser Val Ser Lys Glu Ile Leu Ala Glu Ala
        35                      40                      45

Lys Lys Leu Asn Asp Ala Gln Ala Pro Lys
    50                      55

<210> SEQ ID NO 29
<211> LENGTH: 58
<212> TYPE: PRT
<213> ORGANISM: Staphylococcus aureus

<400> SEQUENCE: 29

Val Asp Asn Lys Phe Asn Lys Glu Gln Gln Asn Ala Phe Tyr Glu Ile
1               5                       10                      15

Leu His Leu Pro Asn Leu Asn Glu Glu Gln Arg Asn Lys Phe Ile Gln
                20                      25                      30

Ser Leu Lys Asp Asp Pro Ser Gln Ser Ala Asn Leu Leu Ala Glu Ala
        35                      40                      45

Lys Lys Leu Asn Asp Ala Gln Ala Pro Lys
    50                      55

<210> SEQ ID NO 30
<211> LENGTH: 58
<212> TYPE: PRT
<213> ORGANISM: Staphylococcus aureus

<400> SEQUENCE: 30

Val Asp Asn Lys Phe Asn Lys Glu Gln Gln Asn Ala Phe Tyr Glu Ile
1               5                       10                      15

Leu His Leu Pro Asn Leu Asn Glu Glu Gln Arg Asn Leu Phe Ile Gln
                20                      25                      30

Ser Leu Lys Asp Asp Pro Ser Gln Ser Ala Asn Leu Leu Ala Glu Ala
        35                      40                      45

Lys Lys Leu Asn Asp Ala Gln Ala Pro Lys
    50                      55

<210> SEQ ID NO 31
<211> LENGTH: 58
<212> TYPE: PRT
<213> ORGANISM: Staphylococcus aureus

<400> SEQUENCE: 31

Val Asp Asn Lys Phe Asn Lys Glu Gln Gln Asn Ala Phe Tyr Glu Ile
1               5                       10                      15

Leu His Leu Pro Asn Leu Asn Glu Gln Arg Asn Arg Phe Ile Gln
                20                      25                      30

Ser Leu Lys Asp Asp Pro Ser Gln Ser Ala Asn Leu Leu Ala Glu Ala
        35                      40                      45

Lys Lys Leu Asn Asp Ala Gln Ala Pro Lys
    50                      55
```

IMMUNOGLOBULIN-BINDING PROTEINS WITH IMPROVED SPECIFICITY

RELATED APPLICATIONS

The present application is a continuation of U.S. patent application Ser. No. 12/462,484, filed on Aug. 4, 2009, which claims the benefit of priority of U.S. Provisional Patent Application No 61/188,549, filed on Aug. 11, 2008, and U.S. Provisional Patent Application No. 61/212,812, filed on Apr. 16, 2009, the entire contents of each of which are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Sep. 6, 2017, is named MCA-925-1US_S-L.txt and is 14,160 bytes in size.

FIELD OF THE INVENTION

The present invention relates to modified immunoglobulin-binding proteins, e.g., *Staphylococcus* protein A, ha mg improved binding specificity for immunoglobulins and methods of making and using the same.

BACKGROUND

Staphylococcal protein A (SpA), is a 42 kDa multi-domain protein from the bacterium *Staphylococcus aureus*. SpA is bound to the bacterial cell wall via its carboxy-terminal cell wall binding region, referred to as the X domain. At the amino-terminal region, it includes five immunoglobulin-binding domains, referred to as E, D, A, B, and C (Sjodhal, *Eur J Biohem.* September; 78(2):471-90 (1977); Uhlen et al., *J Biol Chem.* February 10; 259(3): 1695-702 (1984)). Each of these domains contains approximately 58 amino acid residues and they share 65-90% amino acid sequence idetnity. The Z domain of SpA is an engineered analogue of the B domain of SpA and includes an alanine instead of a glycine residue at position 29.

SpA based reagents have found a widespread use in the field of biotechnology, e.g., in affinity chromatography for capture and purification of antibodies as well as in antibody detection methods. At present, SpA-based affinity media probably are the most widely used affinity media for isolation of monoclonal antibodies and their fragments from different samples including cell culture. Accordingly, various matrices comprising protein A-ligands are commercially available including, for example, ProSep®-vA High Capacity, ProSep® vA Ultra and ProSep® UltraPlus (Millipore) and Protein A Sepharose™, MabSelect™, MabSelect Xtra™ and MabSelect SuRe® (GE Healthcare).

SUMMARY OF THE INVENTION

The present invention provides, at least in part, novel and improved SpA variants which exhibit either decreased or increased binding to a Fab portion of an immunoglobulin compared to the previously known SpA variants, while retaining the ability to bind the Fc portion of the immunoglobulin.

In some embodiments, the present invention provides novel and improved SpA variants which exhibit reduced Fab binding compared to the many commercially available protein-A based reagents which bind Fab, a property which is sometimes undesirable.

In one embodiment, an immunoglobulin-binding domain according to the present invention is based on one or more domains of SpA (i.e., E, D, A, B, C and Z) which are modified to replace at least the amino acid at position 29. In case of the domains E, D, A, B and C, the amino acid at position 29 is a glycine, which is replaced with an amino acid other than alanine or tryptophan. In case of domain Z, the amino acid at position 29 is an alanine, which is replaced with an amino acid other than glycine or tryptophan. In a particular embodiment, the glycine at position 29 is replaced with an amino acid other than alanine, threonine and tryptophan or the alanine at position 29 is replaced with an amino acid other than glycine, threonine and tryptophan.

Accordingly, in one embodiment, an isolated immunoglobulin-binding protein is provided, which comprises at least an E domain of SpA, in which at least the glycine residue at position 29 is replaced with an amino acid residue other than alanine or tryptophan and where the immunoglobulin-binding protein exhibits binding to an Fc portion of an immunoglobulin but exhibits reduced binding to a Fab portion of the immunoglobulin relative to an immunoglobulin-binding protein which includes either alanine or glycine at position 29. In a particular embodiment, the glycine residue at position 29 of the E domain is replaced with an amino acid residue other than alanine, threonine and tryptophan.

In another embodiment, an isolated immunoglobulin-binding protein is provided, which comprises at least a D domain of SpA, in which at least the glycine residue at position 29 is replaced with an amino acid residue other than alanine or tryptophan and where the immunoglobulin-binding protein exhibits binding to an Fc portion of an immunoglobulin but exhibits reduced binding to a Fab portion of the immunoglobulin relative to an immunoglobulin-binding protein which includes alanine or glycine at position 29. In a particular embodiment, the glycine residue at position 29 of the D domain is replaced with an amino acid residue other than alanine, threonine and tryptophan.

In yet another embodiment, an isolated immunoglobulin-binding protein is provided, which comprises at least an A domain of SpA, in which at least the glycine residue at position 29 replaced with an amino acid residue other than alanine or tryptophan and where the immunoglobulin-binding protein exhibits binding to an Fc portion of an immunoglobulin but exhibits reduced binding to a Fab portion of the immunoglobulin relative to an immunoglobulin-binding protein which includes an alanine or glycine at position 29. In a particular embodiment, the glycine residue at position 29 of the A domain is replaced with an amino acid residue other than alanine, threonine and tryptophan.

In another embodiment, an isolated immunoglobulin-binding protein is provided, which comprises at least a B domain of SpA, in which at least the glycine residue at position 29 replaced with an amino acid residue other than alanine or tryptophan and where the immunoglobulin-binding protein exhibits binding to an Fc portion of an immunoglobulin but exhibits reduced binding to a Fab portion of the immunoglobulin relative to an immunoglobulin-binding protein which includes an alanine or glycine at position 29. In a particular embodiment, the glycine residue at position 29 of the B domain is replaced with an amino acid residue other than alanine, threonine and tryptophan.

In yet another embodiment, an isolated immunoglobulin-binding protein is provided, which comprises at least a C domain of SpA, in which at least the glycine residue at position 29 is replaced with an amino acid residue other than alanine or tryptophan and where the immunoglobulin-binding protein exhibits binding to an Fc portion of an immunoglobulin but exhibits reduced binding to a Fab portion of the immunoglobulin relative to an immunoglobulin-binding protein which includes an alanine or glycine at position 29. In a particular embodiment, the glycine residue at position 29 of the C domain is replaced with an amino acid residue other than alanine, threonine and tryptophan.

In another embodiment, an isolated immunoglobulin-binding protein is provided, which comprises at least a Z domain of SpA, in which at least the alanine residue at position 29 replaced with an amino acid residue other than glycine or tryptophan and where the immunoglobulin-binding protein exhibits binding to an Fc portion of an immunoglobulin but exhibits reduced binding to a Fab portion of the immunoglobulin relative to an immunoglobulin-binding protein which includes an alanine or glycine at position 29. In a particular embodiment, the alanine residue at position 29 of the Z domain is replaced with an amino acid residue other than glycine, threonine and tryptophan.

In some embodiments, an immunoglobulin-binding protein according to the present invention includes more than one modified SpA domain or known variants thereof (e.g., more than one of E, D, A, B, C and/or Z and any combinations thereof) where each domain comprises the glycine (i.e. in case of E, D, A, B and C domains) or alanine (i.e., in case of Z domain) at position 29 substituted with another amino acid, e.g., an amino acid other than alanine, glycine or tryptophan. In a particular embodiment, the glycine or alanine at position 29 is replaced with an amino acid other than alanine, glycine, tryptophan and threonine.

In some embodiments, the glycine (G) at position 29 in one or more of isolated E, D, A, B, and C domains or alanine at position 29 in the isolated Z domain is replaced with an amino acid selected from the group consisting of leucine (L), lysine (K), asparagine (N), valine (V), isoleucine (I), serine (S), cysteine (C), methionine (M), phenylalanine (F), tyrosine (Y), glutamic acid (E), glutamine (Q), histidine (H), proline (P), arginine (R), aspartic acid (D) or a functional variant or derivative thereof.

In a particular embodiment, an immunoglobulin-binding protein according to the present invention includes one or more isolated E, D, A, B, C or Z domains, where the one or more isolated domains comprise the glycine residue at position 29 (e.g., in case of E, D, A, B and C domains) or the alanine at position 29 (e.g., in case of Z domain) replaced with an amino acid residue selected from the group consisting of leucine, lysine and arginine or a functional variant, or derivative thereof.

In a yet further embodiment, an immunoglobulin-binding protein according to the invention further includes at least a portion of the carboxy-terminal region of SpA (designated the X domain).

In some embodiments, an immunoglobulin-binding protein according to the present invention further comprises an asparagine, e.g., at position 23, substituted with another amino acid.

In an alternative embodiment, an isolated immunoglobulin-binding protein comprising one or more isolated E, D, A, B, C or Z domains of *Staphyloccocus* protein A is provided, where the one or more isolated domains comprise: (i) at least the glycine residue at position 29 replaced with an amino acid residue other than alanine when the domain is E, D, A, B or C domain or (ii) at least the alanine at position 29 replaced with an amino acid other than glycine when the domain is the Z domain, where the immunoglobulin-binding protein binds an Fc portion of an immunoglobulin and exhibits increased binding to a Fab portion of the immunoglobulin relative to an immunoglobulin-binding protein including alanine at position 29.

In some embodiments, an isolated immunoglobulin-binding protein according to the present invention includes a threonine or a tryptophan at position 29, where immunoglobulin-binding protein binds an Fc portion of an immunoglobulin and exhibits increased binding to a Fab portion of the immunoglobulin relative to an immunoglobulin-binding protein including alanine at position 29. In some embodiments, the Fc portion may be a part of an Fc fusion protein.

The immunoglobulins which are capable of being bound by the various immunoglobulin-binding proteins described herein include one or more of IgG, IgA and IgM.

In other embodiments, a chromatography matrix useful for the isolation of immunoglobulins or antibodies is provided. In one embodiment, a chromatography matrix according to the present invention comprises an isolated immunoglobulin binding protein, as described herein, coupled to a solid support.

Also provided herein are nucleic acid molecules encoding the various immunoglobulin-binding proteins described herein, as well as host cells including such nucleic acid molecules. In some embodiments, a host cell is a prokaryotic cell. In other embodiments, a host cell is a eukaryotic cell.

Additionally, the present invention encompasses a library of polypeptides comprising one or more immunoglobulin-binding proteins described herein, and functional variants thereof. In yet another embodiment, the present invention provides a library of nucleic acid molecules encoding one or more immunoglobulin-binding proteins encompassed by the present invention or encoding functional variants thereof.

Also provided herein are methods of using the immunoglobulin-binding proteins described herein. In some embodiments, a method of affinity purifying one or more immunoglobulins from a sample is provided, which comprises the steps of: (a) providing a sample comprising one or more immunoglobulins; (b) contacting the sample with a chromatography matrix comprising an immunoglobulin binding protein, as described herein, under conditions such that the one or more immunoglobulins bind to the matrix; and recovering the one or more bound immunoglobulins by eluting at a suitable pH.

In various embodiments described herein, the suitable pH at which one or more bound immunoglobulins are eluted is an acidic pH.

BRIEF DESCRIPTION OF THE DRAWINGS

FIG. 1 depicts the nucleic acid sequences for the wild type (wt) IgG binding domains of SpA, represented by SEQ ID NOs:1-5. SEQ ID NO:1 represents the nucleic acid sequence for the wt E domain; SEQ ID NO: 2 represents the nucleic acid sequence for the wt D domain; SEQ ID NO: 3 represents the nucleic acid sequence for the wt A domain; SEQ ID NO: 4 represents the nucleic acid sequence for the wt B domain; and SEQ ID NO: 5 represents the nucleic acid sequence for the wt C domain.

FIG. 2 depicts the nucleic acid sequence for the Z domain of SpA, represented by SEQ ID NO: 6.

FIG. 3 depicts the amino acid sequence alignments of the wild, type (wt) IgG binding domains of SpA (E, D, A, B and C) including a glycine at position 29. SEQ ID NO: 7 represents the amino acid sequence of the wt E domain; SEQ ID NO: 8 represents the amino acid sequence of the wt D domain; SEQ ID NO: 9 represents the amino acid sequence of the wt A domain; SEQ ID NO: 10 represents the amino acid sequence of the wt B domain; and SEQ ID NO: 11 represents the amino acid sequence of the wt C domain.

FIG. 4 depicts the amino acid sequence of the Z domain, represented by SEQ ID NO: 12.

FIG. 6 depicts the nucleic acid sequences for three SpA B domain mutants, in which the glycine at position 29 has been replaced by leucine, lysine or arginine. SEQ ID NO: 13 represents the nucleic acid sequence for the SpA mutant G29L; SEQ ID NO: 14 represents the nucleic acid sequence for the SpA mutant G29K; and SEQ ID NO: 15 represents the nucleic acid sequence for the SpA mutant G29R.

FIG. 7 depicts the amino acid sequences for three SpA B domain mutants, in which the glycine at position 29 has been replaced by leucine, lysine or arginine. SEQ ID NO: 16 represents the amino acid sequence for the SpA B domain mutant G29L; SEQ ID NO: 17 represents the amino acid sequence for the SpA B domain mutant G29K; and SEQ ID NO: 18 represents the amino acid sequence for the SpA B domain mutant G29R.

Figure 8:
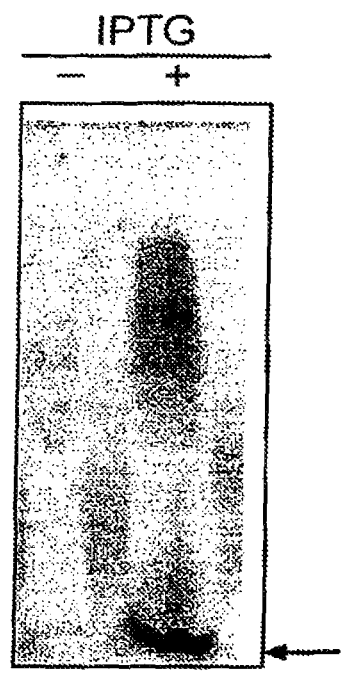

FIG. 8 depicts an exemplary Western Blot experiment in which protein A expression from vector PET11a:8620 in *E. Coli* BL21(DE3) cells was detected using a Chicken IgY anti-protein A antibody.

Figure 9:
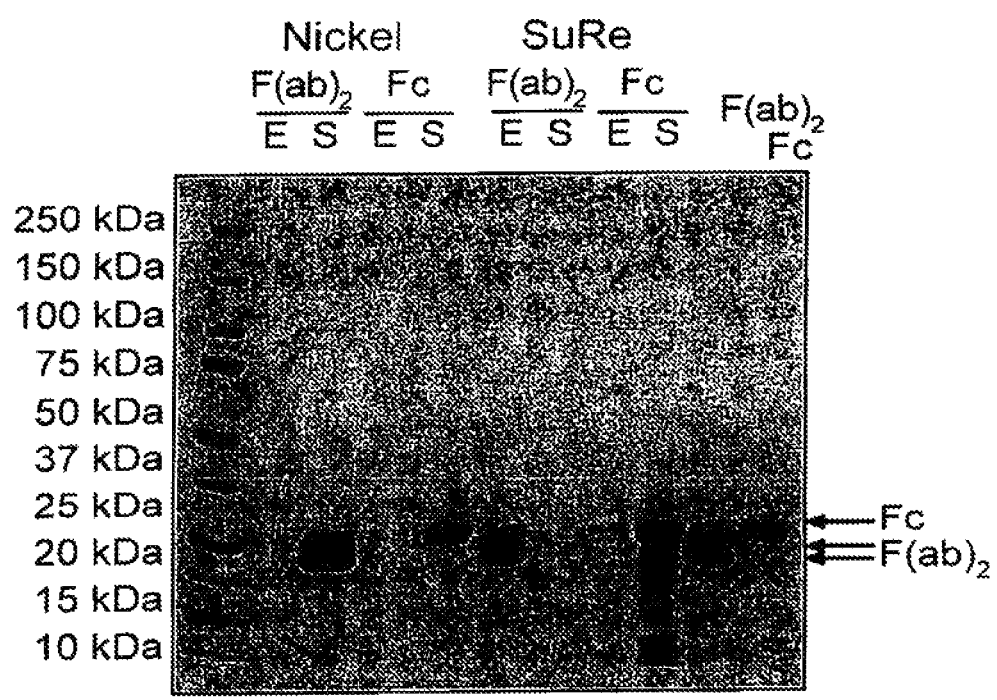

FIG. 9 depicts the results of a representative experiment evaluating the binding of Fc and F(ab)$_2$ portions of an immunoglobulin to nickel resin alone (negative control) or to MabSelect SuRe® chromatography medium (positive control), followed by SDS-PAGE analysis, which is shown. E represents eluate or the bound fraction following chromatography and S represents supernatant or the unbound fraction following chromatography. From left to right: lane 1 depicts a molecular weight marker; lanes 2-5 depict binding of either F(ab)$_2$ (lanes 2(E), 3(S)) or Fc (lanes 4(E), 5(S)) to the nickel resin; lanes 6-9 depict binding of either F(ab)$_2$ (lanes 6(S), 7(E)) or Fc (lanes 8(S), 9(E)) to the MabSelect SuRe®; and lanes 10 and 11 represent F(ab)$_2$ and Fc alone. F(ab)$_2$ runs on an SDS-PAGE as a doublet of about 18 and 20 kDa and Fc runs on an SDS PAGE at about 22 kDa. As shown in lanes 2(E) and 4(E) respectively, both F(ab)$_2$ and Fc exhibit weak to no binding to the nickel resin (negative control). Also, as shown in lane 7(E), F(ab)$_2$ shows binding to the MabSelect SuRe®, while Fc shows significant binding to the MabSelect SuRe® (positive control).

Figure 10:
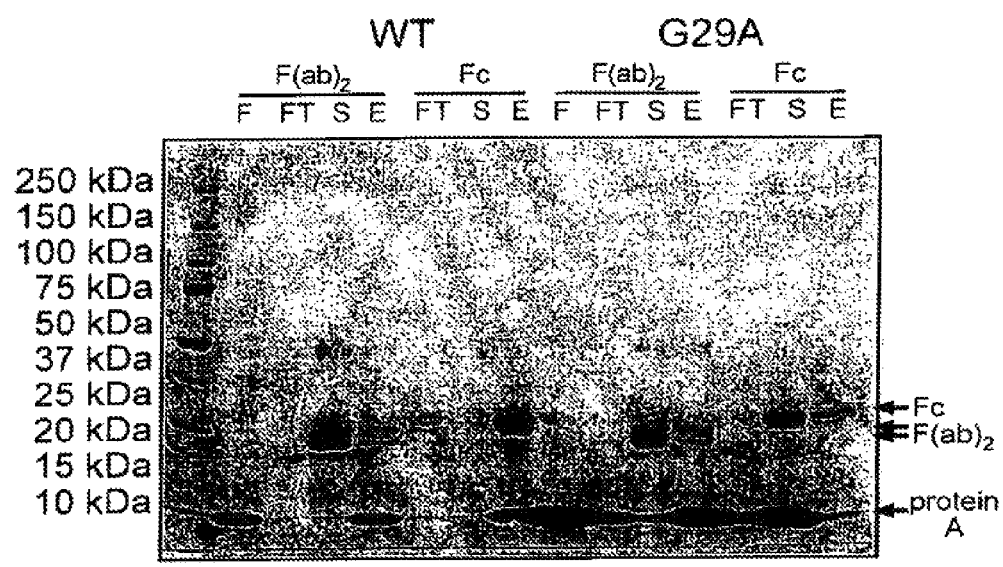

FIG. 10 depicts the results of a representative experiment evaluating the binding of F(ab)$_2$ and Fc portions of an immunoglobulin to His-tagged wild-type SpA (wtSpA) or His-tagged B-domain variant including an alanine instead of glycine at position 29 (G29A) using nickel affinity chromatography followed by SDS-PAGE analysis, which is shown. F represents protein A feed; FT represents protein A flow-through; S represents supernatant following the Fc or Fab binding step (unbound fraction); and E represents elution fraction (bound fraction). From left to right: lane 1 depicts a molecular weight marker; lane 2 depicts the F fraction from the experiment evaluating the binding of wtSpA to F(ab)$_2$ or Fc; lanes 3-5 depict the binding of wtSpA to F(ab)$_2$ in the FT (lane 3), S (lane 4) and E (lane 5) fractions; lanes 6-8 depict the binding of wtSpA to Fc in the FT (lane 6), S (lane 7) and E (lane 8) fractions; lane 9 depicts the F fraction from the experiment evaluating the binding of G29A to F(ab)$_2$ or Fc; lanes 10-12 depict the binding of G29A to F(ab)$_2$ in the FT (lane 10), S (lane 11) and E (lane 12) fractions; and lanes 13-15 depict the binding of G29A to Fc in the FT (lane 13), S (lane 14) and E (lane 15) fractions.

Figure 11:
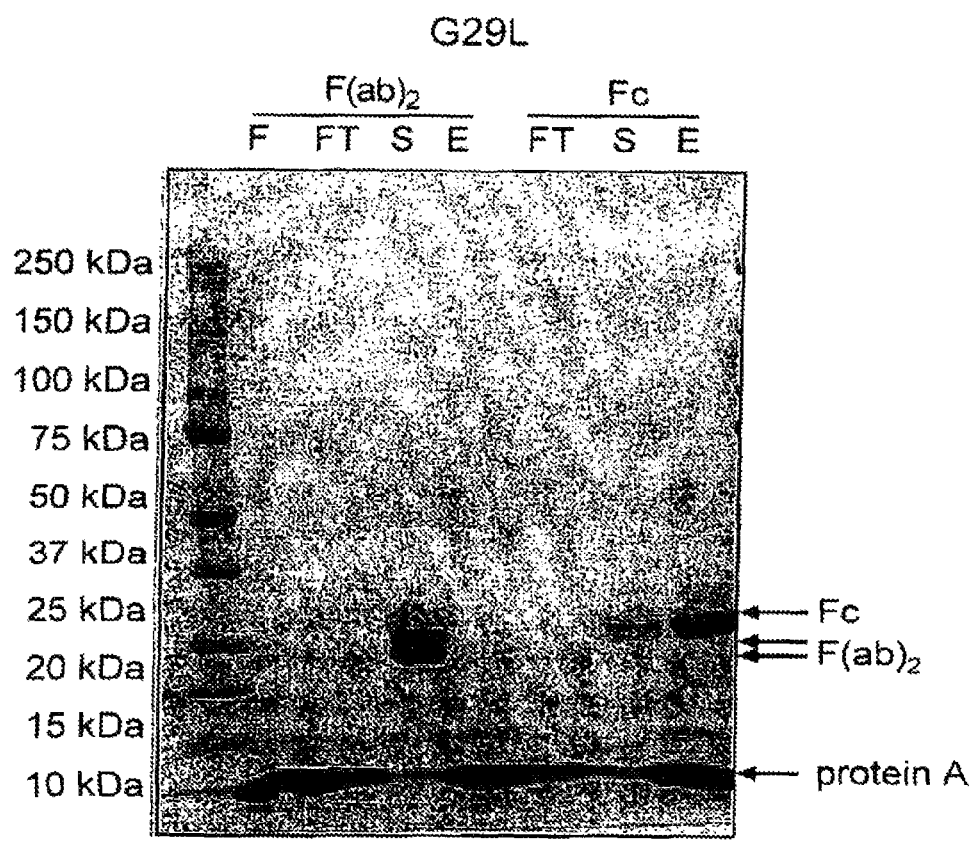

FIG. 11 depicts the results of a representative experiment evaluating the binding of F(ab)$_2$ and Fc portions of an immunoglobulin to a His-tagged B-domain variant including a leucine instead of glycine at position 29 (G29L) using nickel affinity chromatography followed by SDS-PAGE, which is shown. F represents protein A feed; FT represents protein A flow-through; S represents supernatant following the Fc or F(ab)$_2$ binding step (unbound fraction); and E represents elution fraction (bound fraction). From left to right: lane 1 depicts a molecular weight marker; lane 2 depicts the F fraction; lanes 3-5 depict the binding of F(ab)$_2$ to G29L in FT (lane 3), S (lane 4) or F (lane 5) fractions; and lanes 6-8 depict the binding of Fc to G29L in FT (lane 6), S (lane 7) and E (lane 8) fractions.

Figure 12:
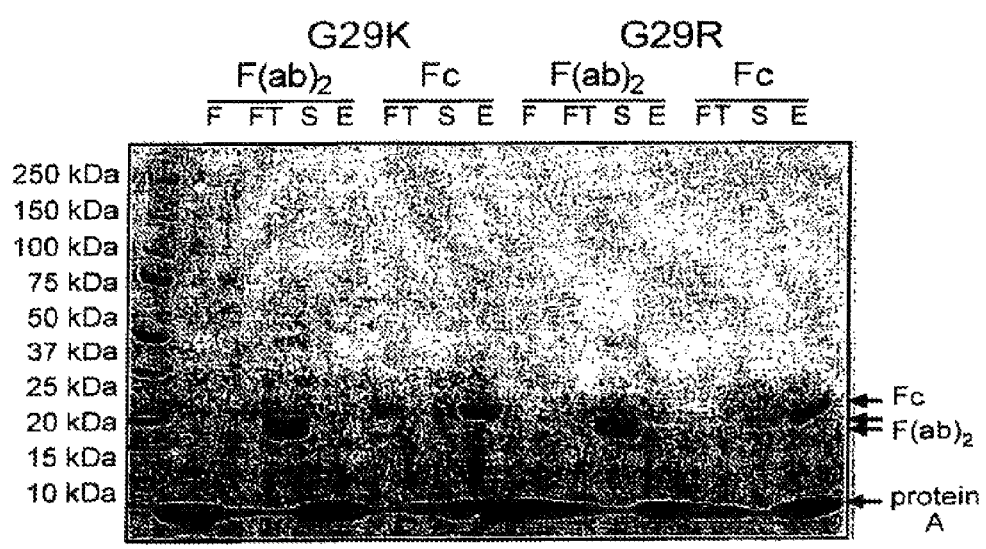

FIG. 12 depicts the results of a representative experiment evaluating the binding of F(ab)$_2$ and Fc portions of an immunoglobulin to a His-tagged B-domain variant including a lysine instead of glycine at position 29 (G29K) and to a His-tagged B-domain variant including an arginine instead of glycine at position 29 (G29R) using nickel affinity chromatography followed by SDS-PAGE, which is shown. F represents protein A feed; FT represents protein A flow-through; S represents supernatant following the Fc or F(ab)$_2$ binding step (unbound fraction); and E represents elution fraction (bound fraction). From left to right: lane 1 depicts a molecular weight marker; lane 2 depicts the F fraction from the experiment evaluating the binding of G29K to F(ab)$_2$ and Fc; lanes 3-5 depict the binding of F(ab)$_2$ to G29K in FT (lane 3), S (lane 4) or E (lane 5) fractions; lanes 6-8 depict the binding of Fc to G29K in FT (lane 6), S (lane 7) and F (lane 8) fractions; lane 9 represents the F fraction from the experiment evaluating the binding of G29R to F(ab)$_2$ and Fc; lanes 10-12 depict the binding of F(ab)$_2$ to G29R in FT (lane 10), S (lane 11) or E (lane 12) fractions; and lanes 13-15 depict the binding of Fc to G29R in FT (lane 13), S (lane 14) and F (lane 15) fractions.

Figure 13A:
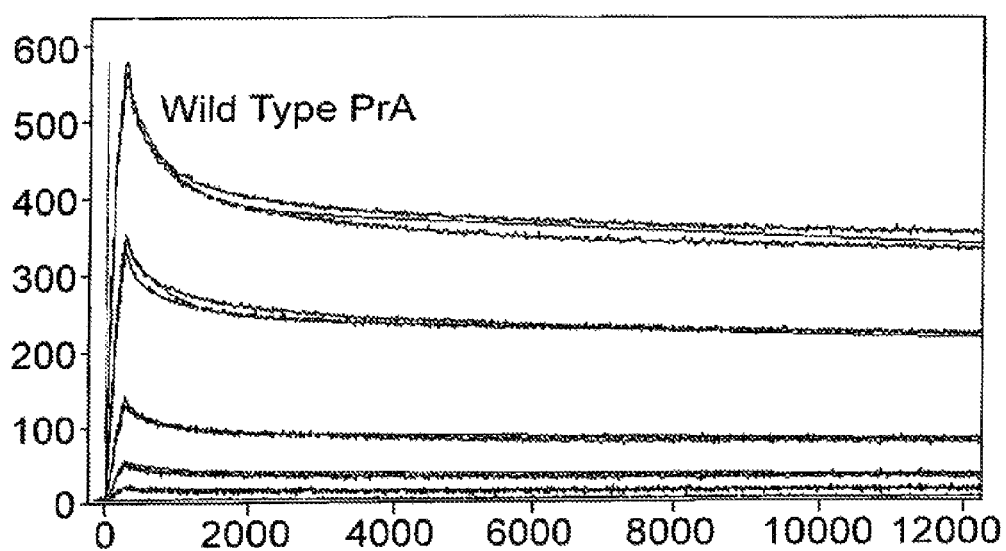
Figure 13B:
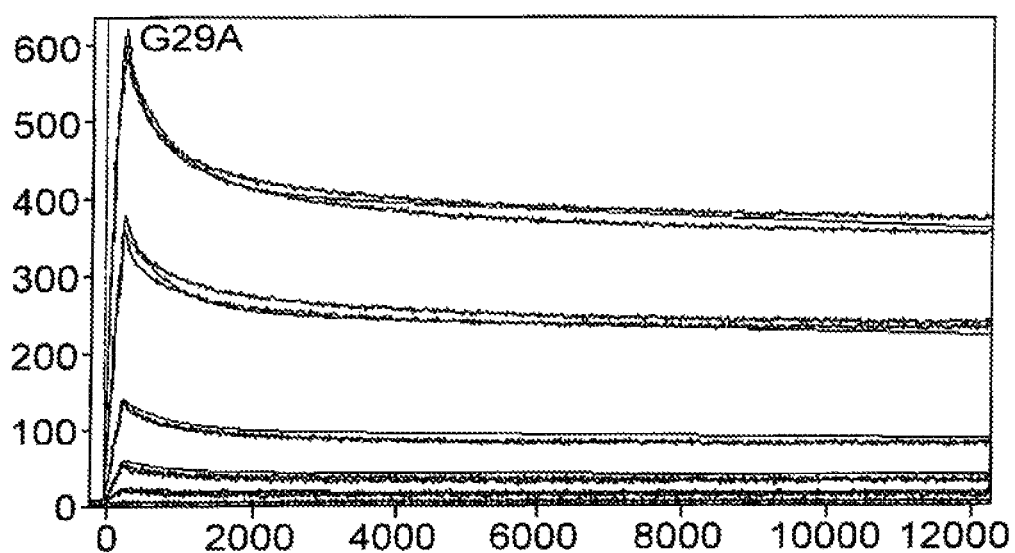
Figure 13C:
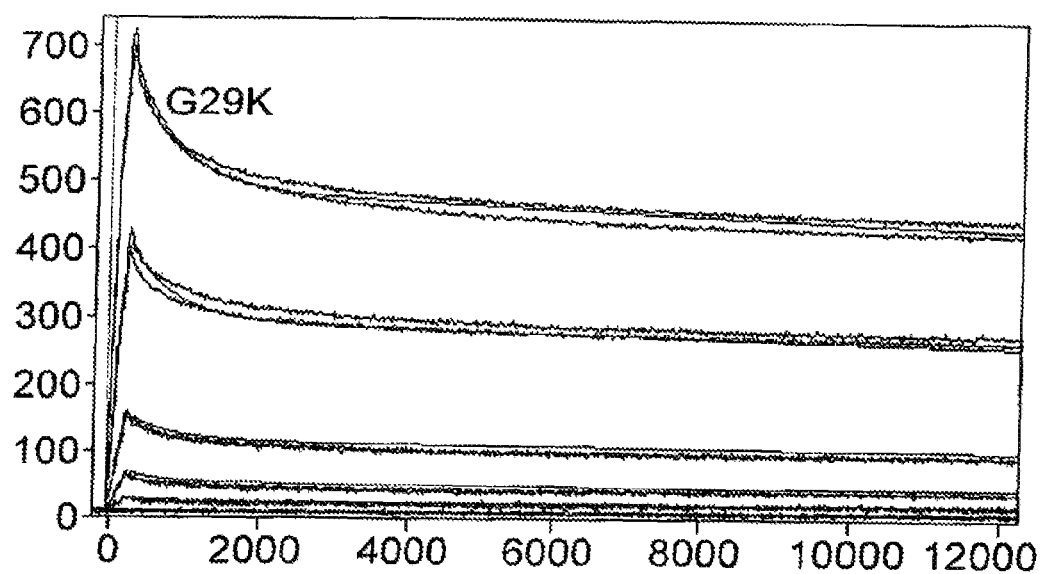
Figure 13D:
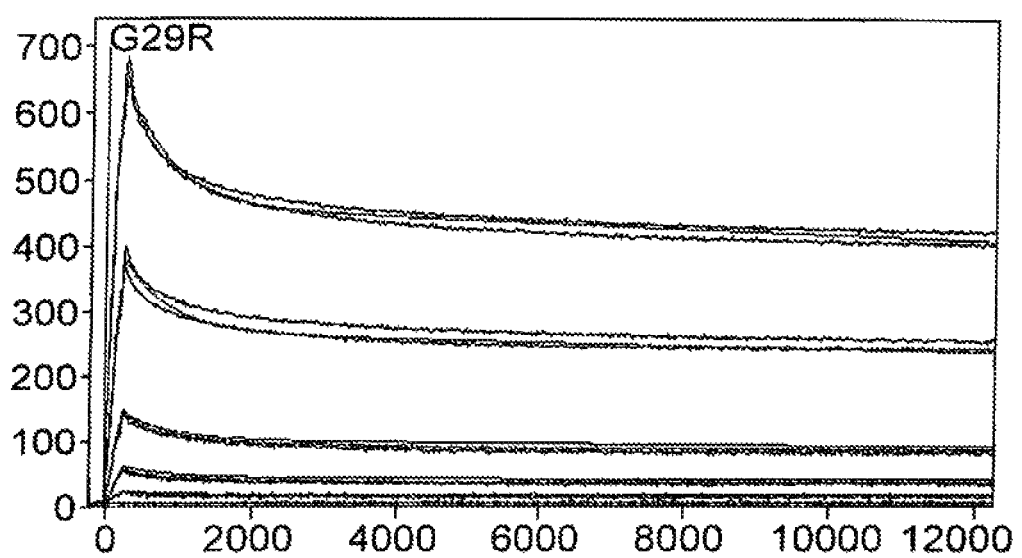
Figure 13E:
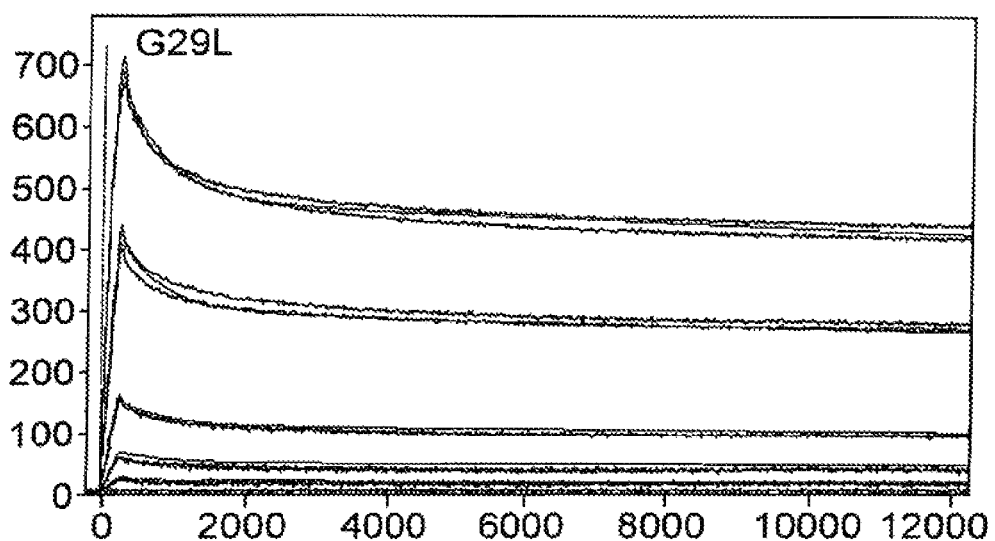

FIGS. 13A-13E depict the results of a representative experiment further evaluating the binding of SpA variants of the invention to an Fc portion of an immunoglobulin using surface plasmon resonance analysis. The figures depict the binding of Fc at concentrations ranging from 45 nM-185 pM to wild type protein A (FIG. 13A) and G29A (FIG. 13B) controls, and to constructs G29K (FIG. 13C), G29R (FIG. 13D), and G29L (FIG. 13E).

Figure 14A:
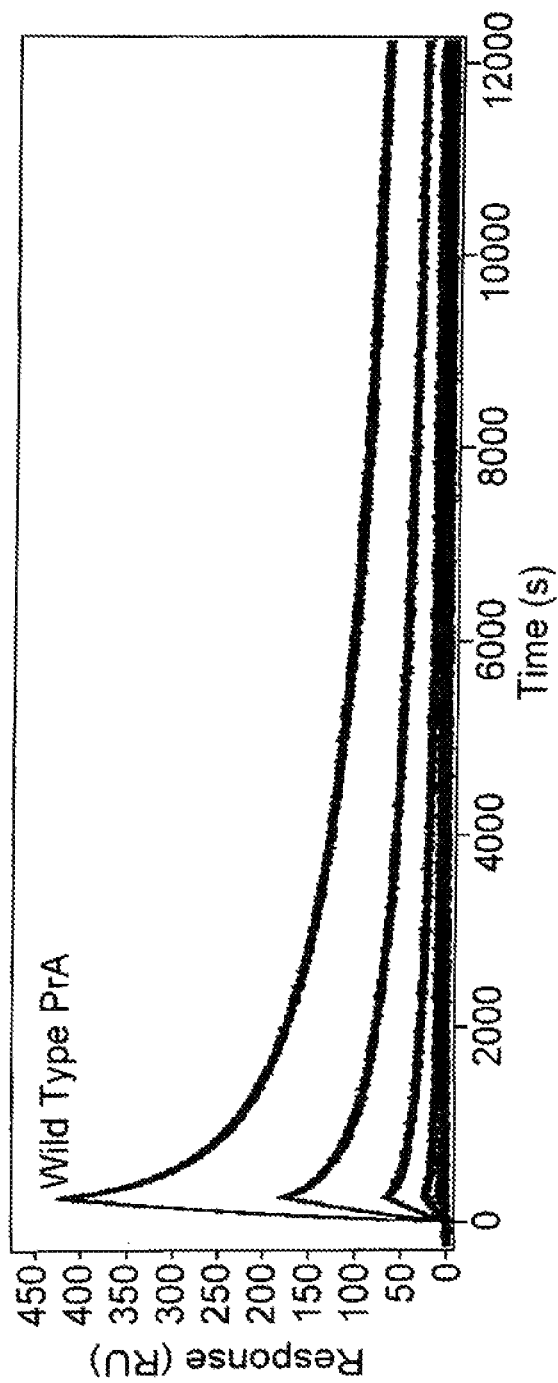
Figure 14B:
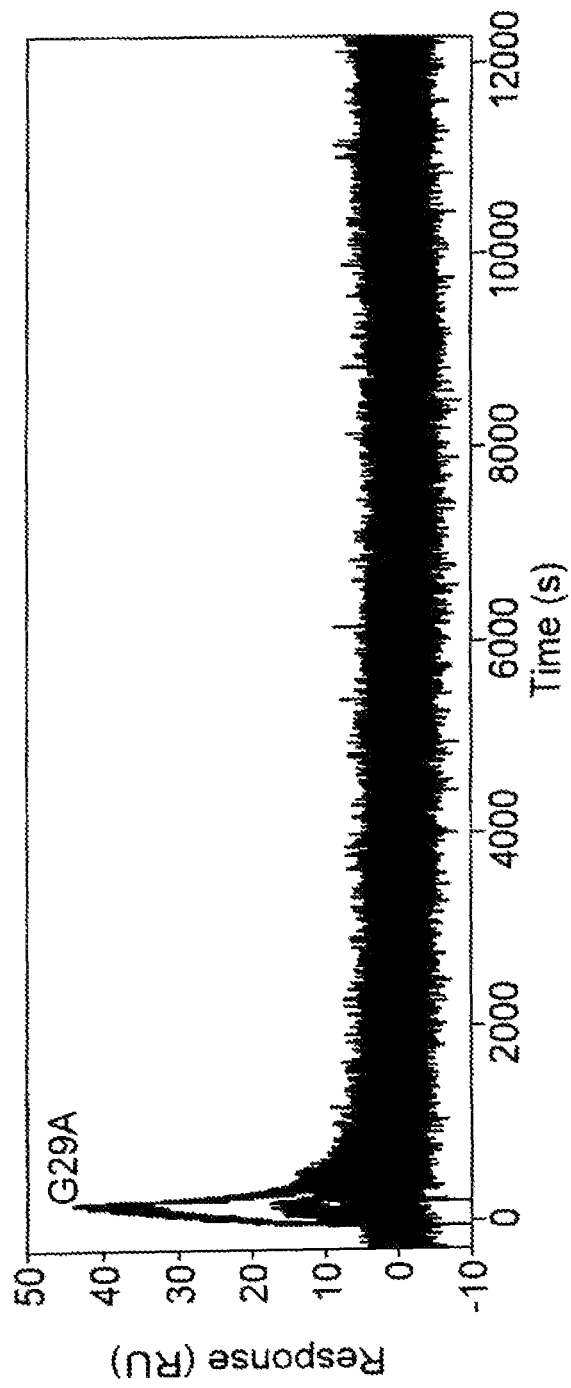
Figure 14C:
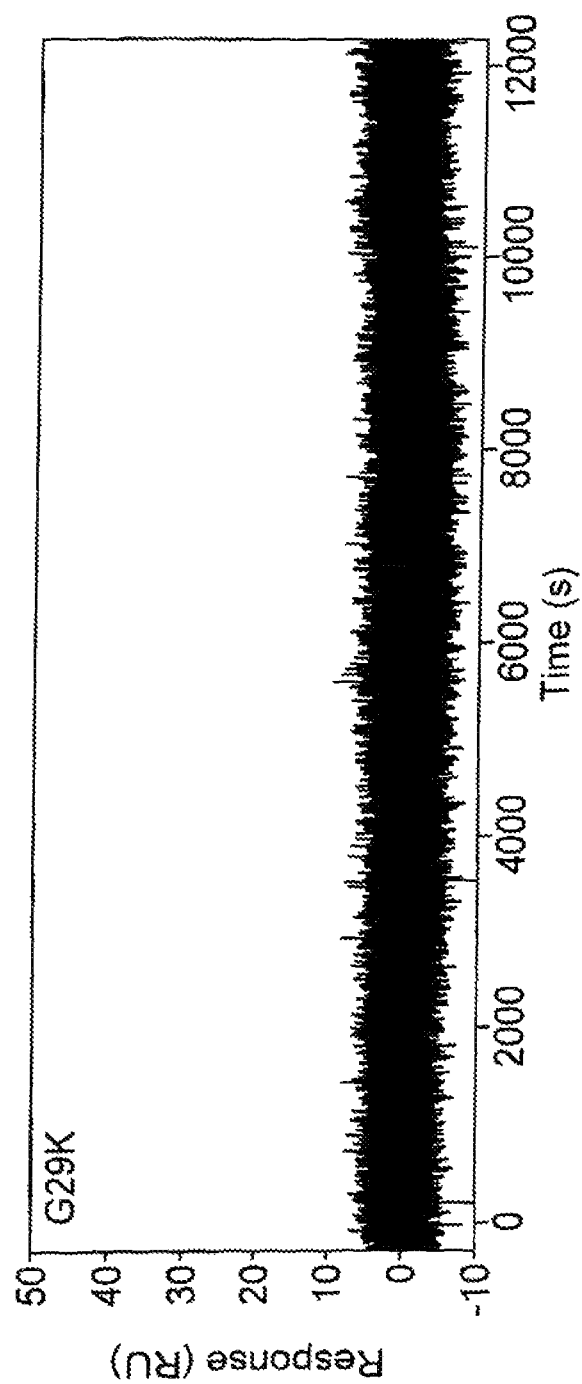
Figure 14D:
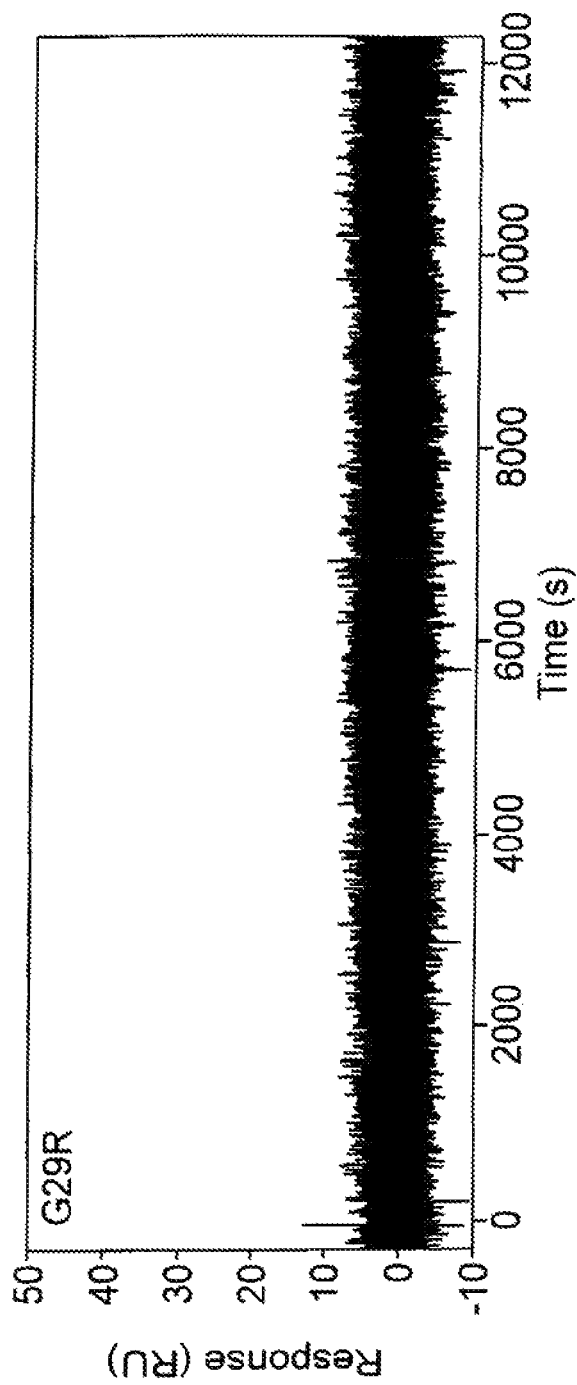
Figure 14E:
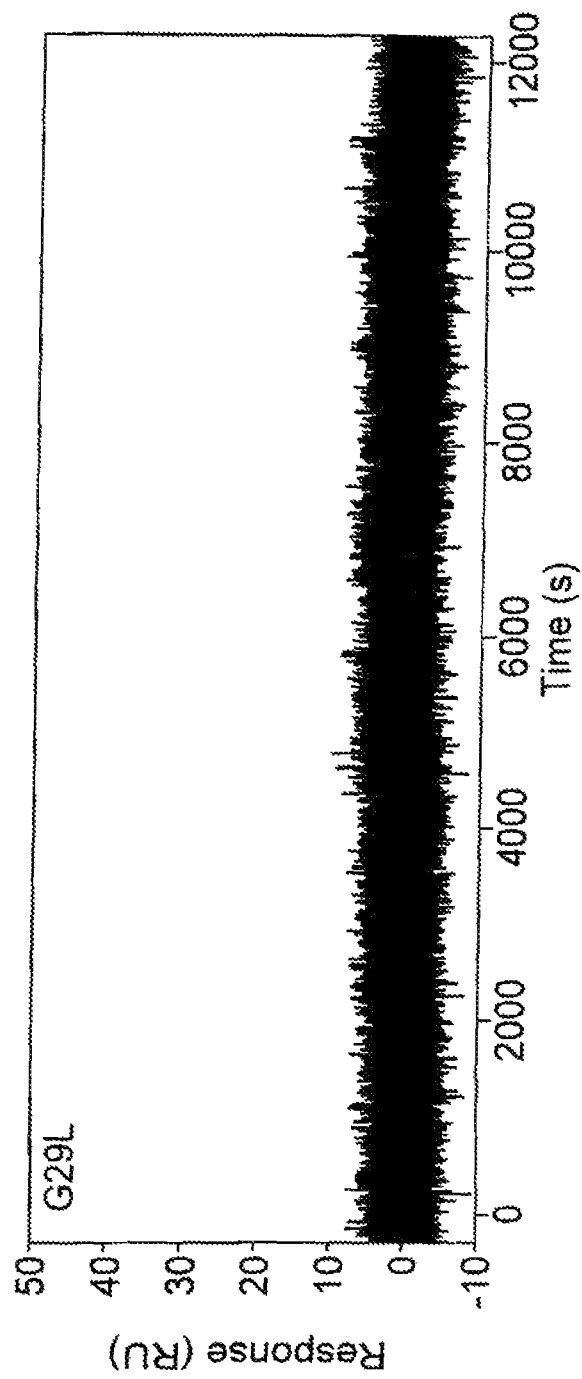

FIGS. 14A-14E depict the results of a representative experiment further evaluating the binding of SpA variants of the invention to an F(ab)$_2$ portion of an immunoglobulin using surface plasmon resonance analysis. The figures depict the binding of F(ab)$_2$ at concentrations ranging from 45 nM-185 pM to the various protein A constructs. Strong binding is observed for wild type protein A (FIG. 14A), and weak binding is seen for the G29A control (FIG. 14B). No binding was detected for G29K (FIG. 14C), G29R (FIG. 14D), and G29L (FIG. 14E)

Figure 15A:
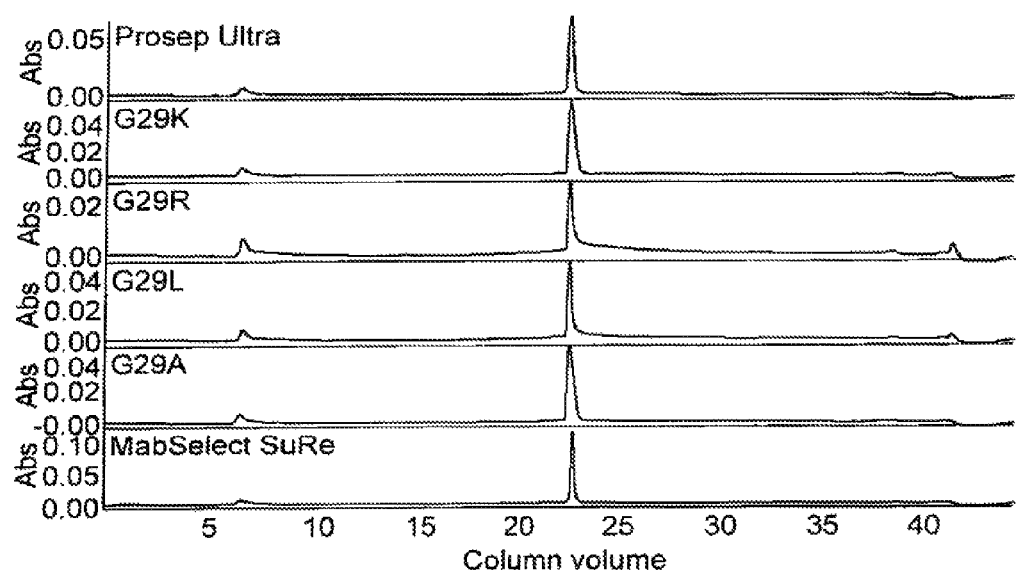
Figure 15B:
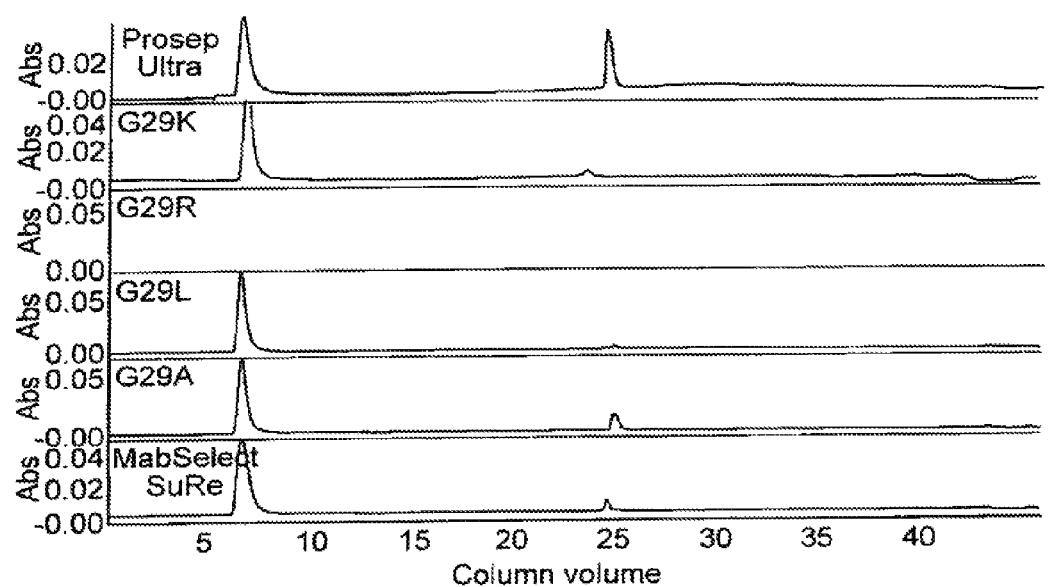

FIGS. 15A-15B depict the results of a representative Fc and Fab pulse experiments for SpA chromatography resins. In FIG. 15A the unbound fraction of Fc appears at 7 column volume (CV), and bound Fc elutes at 23 CV. In FIG. 15B the unbound fraction of F(ab)2 appears at 7 CV, and bound Fc elutes between 23-25 CV.

DETAILED DESCRIPTION OF THE INVENTION

The present invention provides, at least in part, variants of SpA which bind a Fab portion of an immunoglobulin with a lower affinity than the wild-type SpA and variants of SpA previously described, while retaining the ability to bind the Fc portion of an immunoglobulin. In some embodiments, variants of SpA described herein bind a Fab portion of an immunoglobulin with a higher affinity than an SpA having an alanine at position 29.

I. Definitions

In order that the present disclosure may be more readily understood, certain terms are first defined. Additional definitions are set forth throughout the detailed description.

As used herein, the term "immunoglobulin binding protein" refers to an amino acid sequence variant of "SpA" or "protein A of *Staphylococcus aureus*," comprising one or more modified domains of SpA (e.g., one or more of modified E, D, A, B, C or Z) which exhibit reduced binding to a Fab portion of an immunoglobulin or Ig molecule relative to the wild-type SpA (wtSpA) or a known variant domain of SpA Z domain). In some embodiments, an immunoglobulin binding protein of the present invention comprises one or more modified domains E, D, A, B, C or Z, where each domain includes an amino acid substitution at position 29. In the case of domains E, D, B, A or C, the glycine at position 29 is replaced with an amino acid other than alanine or tryptophan and in the case of the Z domain, the alanine at position 29 is replaced with an amino acid other than glycine or tryptophan. In some embodiments, the glycine at position 29 is replaced with an amino acid other than alanine, threonine and tryptophan and the alanine at position 29 is replaced with an amino acid other than glycine, threonine and tryptophan. In some embodiments, amino acid sequence variants may differ from the parent amino acid sequence from which they are derived, in the substitution, deletion and/or insertion of one or more amino acids anywhere within the parent amino acid sequence and including an amino acid residue substitution at least at position 29. In some embodiments, amino acid sequence variants will possess at least about 70%, or at least about 80%, or at least about 85%, or at least about 90%, or at least about 95%, or at least about 96%, or at least about 97%, or at least about 98% identity with the parent sequence (i.e. wt SpA domains or Z domain), where such variants bind the Fc portion of an immunoglobulin, however, exhibit reduced binding to a Fab portion of the immunoglobulin relative to an SpA amino acid sequence which includes a glycine or an alanine at position 29.

In an alternative embodiment, the glycine or alanine at position 29 is replaced with a threonine or a tryptophan, where the immunoglobulin-binding protein binds the Fc portion of an immunoglobulin and exhibits increased binding to a Fab portion of the immunoglobulin relative to an SpA amino acid sequence which includes an alanine at position 29.

The term "sequence identity" means that two nucleotide or amino acid sequences, when optimally aligned, such as by the programs GAP or BESTFIT using default gap weights, share at least 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLAST program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In one embodiment, an immunoglobulin binding protein according to the present invention is based on an isolated domain of wtSpA (i.e., E, D, A, B or C) which includes at least the glycine amino acid residue at position 29 replaced with an amino acid residue other than an alanine or tryptophan, where the immunoglobulin binding protein exhibits reduced binding to a Fab portion of the Ig molecule relative to an immunoglobulin binding protein which includes an alanine or glycine at position 29. In another embodiment, the immunoglobulin binding protein according to the invention is based on a Z domain of SpA which includes at least the alanine residue at position 29 replaced with an amino acid other than glycine or tryptophan. In another embodiment, the glycine residue at position 29 (i.e., in case of E, D, A, B and C domains) is replaced with an amino acid residue other than alanine, threonine and tryptophan or the alanine residue at position 29 (i.e., in case of the Z domain) is replaced with an amino acid residue other than glycine, threonine and tryptophan, where the immunoglobulin-binding protein exhibit reduced binding to a Fab portion of an Ig molecule relative to an immunoglobulin-binding protein which includes alanine or glycine at position 29.

In some embodiments, an immunoglobulin binding protein according to the present invention includes at least two or more, or at least three or more, or at least four or more, or at least five or more of domains designated E, D, A, B, C and Z, where each of the two or more, or three or more, or four or more, or five or more of the domains include at least a glycine (e.g., in the case of domains E, D, A, B and C) or alanine (in the case of Z domain) at position 29 substituted with an amino acid residue other than a glycine, alanine, tryptophan and threonine and where the immunoglobulin binding protein exhibits reduced binding to a Fab portion of the Ig molecule relative to an immunoglobulin binding protein which includes a glycine or alanine at position 29.

In some embodiments, an immunoglobulin binding protein according to the invention includes multimers of the same domain (e.g., two or more of E domain; two or more of D domain; two or more of A domain; two or more of B domain; two or more of C domain; and two or more of Z domain), where each of the monomers includes at least a glycine or alanine at position 29 substituted with an amino acid other than glycine, alanine, tryptophan and threonine, where the immunoglobulin binding protein exhibits reduced binding to a Fab portion of the Ig molecule relative to an immunoglobulin binding protein which includes an alanine or glycine at position 29.

Suitable amino acids to replace glycine or alanine at position 29 include any of the standard naturally occurring amino acids, excluding glycine, alanine and tryptophan and in certain embodiments, excluding glycine, alanine, tyrtophan and threonine. In some embodiments, the naturally occurring amino acids include one of arginine and leucine. In other embodiments, the naturally occurring amino acids include one of lysine, arginine, leucine, cysteine, aspartic acid, glutamic acid, glutamine, phenylalanine, histidine, isoleucine, methionine, asparagine, proline, serine, valine and tyrosine. Non-naturally occurring amino acids and amino acid derivatives which are well known in the art could also be used to replace the glycine or alanine at position 29.

Exemplary SpA domain modifications are shown in Table I. Immunoglobulin binding proteins encompassed by the present invention may include any combinations of one or more, two or more, three or more, four or more, five or more, or six or more of domains (E, D, A, B, C and Z), where each domain includes a modification at position 29, and where the glycine or alanine at position 29 is replaced with an amino acid residue other than glycine, alanine, and tryptophan and in some embodiments, other than glycine, alanine, tryptophan and threonine. Also encompassed by the present invention are immunoglobulin binding proteins which include two or more domains of the same kind (e.g., two or more E domains; two or more D domains; two or more A domains; two or more B domains; two or more C domains; and two or more Z domains), where each domain includes a modification at position 29, where the amino acid residue at position 29 is replaced with an amino acid residue other than glycine, alanine and tryptophan and in some embodiments, other than glycine, alanine, tryptophan and threonine.

TABLE I

| SpA domains including modifications | Designation |
| --- | --- |
| E, D, A, B, C or Z or domain-glycine 29 or alaine 29 replaced with arginine | E-G29R |
| | D-G29R |
| | A-G29R |
| | B-G29R |
| | C-G29R |
| | Z-A29R |
| E, D, A, B, C or Z domain-glycine 29 or alanine 29 replaced with asparagine | E-G29N |
| | D-G29N |
| | A-G29N |
| | B-G29N |
| | C-G29N |
| | Z-A29N |
| E, D, A, B, C or Z domain-glycine 29 or alanine 29 replaced with aspartic acid | E-G29D |
| | D-G29D |
| | A-G29D |
| | B-G29D |
| | C-G29D |
| | Z-A29D |
| E, D, A, B, C or Z domain-glycine 29 or alanine 29 replaced with cysteine | E-G29C |
| | D-G29C |
| | A-G29C |
| | B-G29C |
| | C-G29C |
| | Z-A29C |
| E, D, A, B, C or Z domain-glycine 29 or alanine 29 replaced with glutamine | E-G29Q |
| | D-G29Q |
| | A-G29Q |
| | B-G29Q |

TABLE I-continued

| SpA domains including modifications | Designation |
| --- | --- |
| | C-G29Q |
| | Z-A29Q |
| E, D, A, B, C or Z domain-glycine 29 or alanine 29 replaced with glutamic acid | E-G29E |
| | D-G29E |
| | A-G29E |
| | B-G29E |
| | C-G29E |
| | Z-A29E |
| E, D, A, B, C or Z domain-glycine 29 or alanine 29 replaced with histidine | E-G29H |
| | D-G29H |
| | A-G29H |
| | B-G29H |
| | C-G29H |
| | Z-A29H |
| E, D, A, B, C or Z domain-glycine 29 or alanine 29 replaced with isoleucine | E-G29I |
| | D-G29I |
| | A-G29I |
| | B-G29I |
| | C-G29I |
| | Z-A29I |
| E, D, A, B, C or Z domain-glycine 29 or alanine 29 replaced with leucine | E-G29L |
| | D-G29L |
| | A-G29L |
| | B-G29L |
| | C-G29L |
| | Z-A29L |
| E, D, A, B, C or Z domain-glycine 29 or alanine 29 replaced with lysine | E-G29K |
| | D-G29K |
| | A-G29K |
| | B-G29K |
| | C-G29K |
| | Z-A29K |
| E, D, A, B, C or Z domain-glycine 29 or alanine 29 replaced with methionine | E-G29M |
| | D-G29M |
| | A-G29M |
| | B-G29M |
| | C-G29M |
| | Z-A29M |
| E, D, A, B, C or Z domain-glycine 29 or alanine 29 replaced with phenylalanine | E-G29F |
| | D-G29F |
| | A-G29F |
| | B-G29F |
| | C-G29F |
| | Z-A29F |
| E, D, A, B, C or Z domain-glycine 29 or alanine 29 replaced with proline | E-G29P |
| | D-G29P |
| | A-G29P |
| | B-G29P |
| | C-G29P |
| | Z-A29P |
| E, D, A, B, C or Z domain-glycine 29 or alanine 29 replaced with serine | E-G29S |
| | D-G29S |
| | A-G29S |
| | B-G29S |
| | C-G29S |
| | Z-A29S |
| E, D, A, B, C or Z domain-glycine 29 or alanine 29 replaced with threonine | E-G29T |
| | D-G29T |
| | A-G29T |
| | B-G29T |
| | C-G29T |
| | Z-A29T |
| E, D, A, B, C or Z domain-glycine 29 or alanine 29 replaced with tyrosine | E-G29Y |
| | D-G29Y |
| | A-G29Y |
| | B-G29Y |
| | C-G29Y |
| | Z-A29Y |
| E, D, A, B, C or Z domain-glycine 29 or alanine 29 replaced with valine | E-G29V |
| | D-G29V |
| | A-G29V |
| | B-G29V |
| | C-G29V |
| | Z-A29V |

As used interchangeably herein, the terms "E domain," "E domain of SpA," and "E domain of *Staphylococcus* protein A," refer to the polypeptide whose amino acid sequence is set forth in SEQ ID NO:7 or that encoded by, e.g., the nucleotide sequence set forth in SEQ ID NO: 1. The "E domain" is a 51 amino acid polypeptide that folds into a three-helix bundle structure. It is capable of binding Fc via residues on the surface of helices 1 and 2, or to Fab via residues on the surface of helices 2 and 3. In some embodiments, an E domain according to the invention is at least 70% identical, or at least 80% identical, or at least 90% identical or at least 95% or more identical in sequence to the amino acid sequence set forth in SEQ ID NO:7.

As used interchangeably herein, the terms "D domain," "D domain of SpA," and "D domain of *Staphylococcus* protein A," refer to the polypeptide whose amino acid sequence is set forth in SEQ ID NO: 8 or that encoded by e.g., the nucleotide sequence set forth in SEQ ID NO: 2. The "D domain" is a 61 amino acid polypeptide that folds into a three-helix bundle structure. It is capable of Fc binding via residues on the surface of helices 1 and 2, or to Fab via residues on the surface of helices 2 and 3. In some embodiments, a D domain according to the invention is at least 70% identical, or at least 80% identical, or at least 90% identical or at least 95% or more identical in sequence to the amino acid sequence set forth in SEQ ID NO: 8.

As used interchangeably herein, the terms "A domain," "A domain of SpA," and "A domain of *Staphylococcus* protein A," refer to the polypeptide whose amino acid sequence is set forth in SEQ ID NO: 3 or that encoded by, e.g., the nucleotide sequence set forth in SEQ ID NO: 9. The "A domain" is a 58 amino acid polypeptide that folds into a three-helix bundle structure. It is capable of Fc binding via residues on the surface of helices 1 and 2, or to Fab via residues on the surface of helices 2 and 3. In some embodiments, an A domain according to the invention is at least 70% identical, or at least 80% identical, or at least 90% identical or at least 95% or more identical in sequence to the amino acid sequence set forth in SEQ ID NO: 3.

As used interchangeably herein, the terms "B domain," "B domain of SpA," and "B domain of *Staphylococcus* protein A," refer to the polypeptide whose amino acid sequence is set forth in SEQ ID NO: 10 or that encoded by, e.g., the nucleotide sequence set forth in SEQ ID NO: 4. The "B domain" is a 58 amino acid polypeptide that folds into a three-helix bundle structure. It is capable of Fc binding via residues on the surface of helices 1 and 2, or to Fab via residues on the surface of helices 2 and 3. In some embodiments, a B domain according to the invention is at least 70% identical, or at least 80% identical, or at least 90% identical or at least 95% or more identical in sequence to the amino acid sequence set forth in SEQ ID NO: 10.

As used interchangeably herein, the terms "C domain," "C domain of SpA," and "C domain of *Staphylococcus* protein A," refer to the polypeptide whose amino acid sequence is set forth in SEQ ID NO: 11 or that encoded by, e.g., the nucleotide sequence set forth in SEQ ID NO: 5. The "C domain" is a 58 amino acid polypeptide that folds into a three-helix bundle structure. It is capable of Fc binding via residues on the surface of helices 1 and 2, or to Fab via residues on the surface of helices 2 and 3. In some embodiments, a C domain according to the invention is at least 70% identical, or at least 80% identical, or at least 90% identical or at least 95% or more identical in sequence to the amino acid sequence set forth in SEQ ID NO: 11.

As used interchangeably herein, the terms "Z domain," "Z domain of SpA" and "Z domain of protein A," refer to the three helix, 59 amino acid polypeptide that is a variant of the B domain of protein A. The amino acid sequence of the Z domain is set forth in SEQ ID NO: 12. An exemplary Z domain is described in Nilsson et al., *Protein Engng.*, 1:107-113 (1997), the entire contents of which are incorporated by reference herein.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins.

The term "antigen-binding fragment" refers to a polypeptide portion of an immunoglobulin or antibody that binds an antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', $F(ab')_2$, Fv, single chains, and single-chain antibodies.

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA- RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In a particular embodiment, a nucleic acid molecule comprises a nucleotide sequence encoding a variant of SpA.

As used herein, the term "reduced binding" refers to any decrease in binding to a Fab (or F(ab)$_2$) portion of an immunoglobulin molecule by an immunoglobulin binding protein according to the present invention relative to an immunoglobulin binding protein which includes an alanine or glycine amino acid residue at position 29. For example, binding to a Fab portion may be decreased by about 10%, or about 20%, or about 30%, or about 40%, or about 50%, or about 60%, or about 70%, or about 80%, or about 90%, or about 95%, or about 96%, or about 97%, or about 98%, or about 99% or more, relative to an immunoglobulin binding protein which includes a glycine or an alanine amino acid residue at position 29. In some embodiments, binding to a Fab portion of an immunoglobulin molecule is reduced by at least 50% or more relative to binding by an immunoglobulin protein which includes a glycine or alanine at position 29. In another embodiment, binding to a Fab portion of an inuramoglobulin molecule is reduced by at least 70% or more. In yet another embodiment, binding to a Fab portion of an immunoglobulin molecule is reduced by at least 90% or more, or at least 95% or more, or at least 99% or more. In one embodiment, binding to a Fab portion of an immunoglobulin molecule is undetectable using conventional techniques in the art and those described herein. Binding to an immunoglobulin molecule can be detected using well known techniques including those described herein and including but not limited to, for example, affinity chromatography and surface plasmon resonance analysis. In some embodiments, an immunoglobulin binding protein encompassed by the present invention binds the Fc portion of an immunoglobulin molecule with a dissociation constant of at least about $10^{-8}$ M for a single IgG binding domain, or about $10^{-11}$ M for 5 tandem IgG binding domains. In other embodiments, an immunoglobulin binding protein according to the invention binds to the Fab portion of an immunoglobulin molecule with a dissociation constant of about $10^{-5}$ M for a single immunoglobulin binding domain or about $10^{-6}$ for intact protein A with five tandem binding domains.

As used herein, the term "increased binding" refers to any increase in binding to a Fab (or F(ab)$_2$) portion of an immunoglobulin molecule by an immunoglobulin binding protein according to the present invention relative to an immunoglobulin binding protein which includes an alanine amino acid residue at position 29. For example, binding to a Fab portion may be increased by about 10%, or about 20%, or about 30%, or about 40%, or about 50%, or about 60%, or about 70%, or about 80%, or about 90%, or about 95%, or about 96%, or about 97%, or about 98%, or about 99% or more, relative to an immunoglobulin binding protein which includes an alanine amino acid residue at position 29. In some embodiments, binding to a Fab portion of an immunoglobulin molecule is increased by at least 50% or more relative to binding by an immunoglobulin protein which includes an alanine at position 29. In another embodiment, binding to a Fab portion of an immunoglobulin molecule is increased by at least 70% or more relative to the Fab binding by an immunoglobulin binding protein which includes an alanine at position 29. In yet another embodiment, binding to a Fab portion of an immunoglobulin molecule increased by at least 90% or more, or at least 95% or more, or at least 99% or more relative to the Fab binding by an immunoglobulin binding protein which includes an alanine at position 29. In exemplary embodiments, an immunoglobulin binding protein which exhibits increased Fab binding relative to an immunoglobulin binding protein including an alanine at position 29, includes a threonine or a tryptophan at position 29. Binding to an immunoglobulin molecule can be detected using well known techniques including those described herein and including but not limited to, for example, affinity chromatography and surface plasmon resonance analysis.

The term "Fc-binding," "binds to an Fc portion" or "binding to an Fc portion" refers to the ability of an immunoglobulin-binding protein described herein, to bind to the crystallizable part (Fc) of an antibody. In some embodiments, an immunoglobulin-binding protein according to the present invention binds an Fc portion of an antibody (e.g., human IgG1, IgG2 or IgG4) with an affinity of at least $10^{-7}$ M, or at least $10^{-8}$ M, or at least $10^{-9}$ M.

The term "affinity separation," or "affinity purification," as used herein, refers to any purification or assaying technique which involves the addition of a sample containing a target analyte (e.g., an immunoglobulin) to a solid support which carries on it an immunoglobulin-binding protein, as described herein.

The term "chromatography," as used herein, refers to any kind of technique which separates the analyte (e.g., an immunoglobulin) to be measured from other molecules in the mixture and allows it to be isolated.

The term "affinity chromatography," as used herein, refers to a mode of chromatography where the analyte to be separated is isolated by its interaction with a molecule (e.g., an immunoglobulin binding protein) which specifically interacts with the analyte.

II. SpA Structure and Immunoglobulin Binding Sites

SpA is about a 42-kDa protein derived from the bacterium *Staphylococcus aureus* and contains five tandem highly homologous extracellular immunoglobulin (Ig)-binding domains at the N-terminus, designated E, D, A, B and C. Each extracellular domain of SpA possesses distinct Ig-binding sites. One site is for Fcγ (the constant region of IgG class of Ig) and the other is for the Fab portion of certain Ig molecules (the portion of the Ig that is responsible for antigen recognition). It has been reported that each of the domains contains a Fab binding site. The non-Ig binding portion of SpA is located at the C-terminus and is designated the X region or X-domain.

The cloning of the gene encoding SpA is described in U.S. Pat. No. 5,151,350, the entire contents of which are incorporated by reference herein in their entirety.

III. Generation and Expression of SpA Variants

The SpA variants of the present invention can be made using any suitable methods known in the art. For example, standard techniques for site-directed mutagenesis of nucleic acids may be used such as those described, for example, in the laboratory manual entitled Molecular Cloning by Sambrook, Fritsch and Maniatis. Additionally, standard molecular biology techniques involving polymerase chain reaction (PCR) mutagenesis may be used.

In some embodiments, SpA variants are generated using standard genetic engineering techniques. For example, a nucleic acid molecule encoding a domain of SpA or portions thereof can be cloned into a suitable vector for expression in an appropriate host cell. Suitable expression vectors are well known in the art and typically include the necessary elements for the transcription and translation of the variant SpA coding sequence.

SpA variants described herein may also be synthesized chemically from amino acid precursors for fragments using methods well known in the art, including solid phase peptide synthetic methods such as the Boc (tert-butyloxycarbonyl) or Fmoc (9-fluorenylmethyloxy carbonyl) approaches (see, e.g., U.S. Pat. Nos. 6,060,596; 4,879,378; 5,198,531; 5,240,680).

Expression of SpA variants can be accomplished in cells from eukaryotic hosts such as yeasts, insects or mammals, or in prokaryotic host cells, e.g., bacteria such as E. coli.

In some embodiments, SpA variants may be expressed on the surface of a bacteriophage such that each phage contains a DNA sequence that codes for an individual SpA variant displayed on the phage surface. In this approach, a library of SpA variants are made by synthesizing random or semi random oligonucleotides at selected positions in the SpA sequence chosen to generate a variety of amino acids at these positions. The encoding DNA is inserted into an appropriate phage vector, packaged into a phage particle and used to infect a suitable bacterial host. Each of the sequences is thus cloned in one phage vector and the SpA variant of interest (e.g., having a mutation at position 29) can be selected by finding those phage that bind to Fc but do not bind to Fab (e.g., by a method known as panning). The phages recovered in this way can be amplified and the selection repeated. Also, the phages can be isolated and the nucleotide sequence encoding selected SpA variants determined by nucleotide sequencing.

IV. Binding of SpA Variants to Fc and Fab

Following generation of the SpA variants, the binding specificity of the SpA variants to Fab or Fc portions of an immunoglobulin is determined using standard techniques in the art and those described herein.

For example, the SpA variant may be constructed with a histidine tag(($His)_6$-tag) for immobilization by nickel affinity chromatography. The nickel-bound SpA can then be tested for Fc and Fab binding by adding appropriate fragments to the resin. Unbound material is washed away, and Fc and Fab are detected in the elution sample by gel electrophoresis.

Alternatively, Fc and Fab binding can be measured by surface plasmon resonance analysis. The SpA variant is immobilized on a chip using amine-reactive chemistry, and Fc or Fab fragment is flowed over the chip. If Fc or Fab binds, an increase in the surface plasmon resonance signal is observed.

SpA can also be immobilized on chromatography beads. Fc or Fab binding is observed by comparing the flow-through and elution peaks for the SpA resin.

V. Use of SpA and Variants thereof for Making Chromatography Matrices

The present invention also provides a method of preparing a chromatography matrix comprising at least one immunoglobulin-binding protein with affinity for the Fc part of an antibody and having reduced or no affinity for the Fab portion of the antibody. In one embodiment, such a method comprises: (a) providing a nucleic acid sequence encoding an isolated SpA domain (e.g., E, D, A, B, C or Z); (b) mutating the nucleic acid sequence to encode for a variant protein where at least the glycine at position 29 has been replaced by an amino acid other than alanine or tryptophan; (c) expressing the variant protein in a host cell (e.g., a suitable prokaryotic cell or a eukaryotic cell); (d) recovering the variant protein from the host cell; and (e) coupling the variant protein to a solid support.

Solid support matrices include, but are not limited to, controlled pore glass, agarose, methacrylate, and polystyrene. The protein can be coupled to the matrix, for example, by amine reactive or thiol reactive chemistry.

This invention is further illustrated by the following examples which should not be construed as limiting. The contents of all references, patents and published patent applications cited throughout this application, as well as the Figures, are incorporated herein by reference.

EXAMPLES

Example 1

Construction of Vectors Containing SpA Variants

Figure 5:
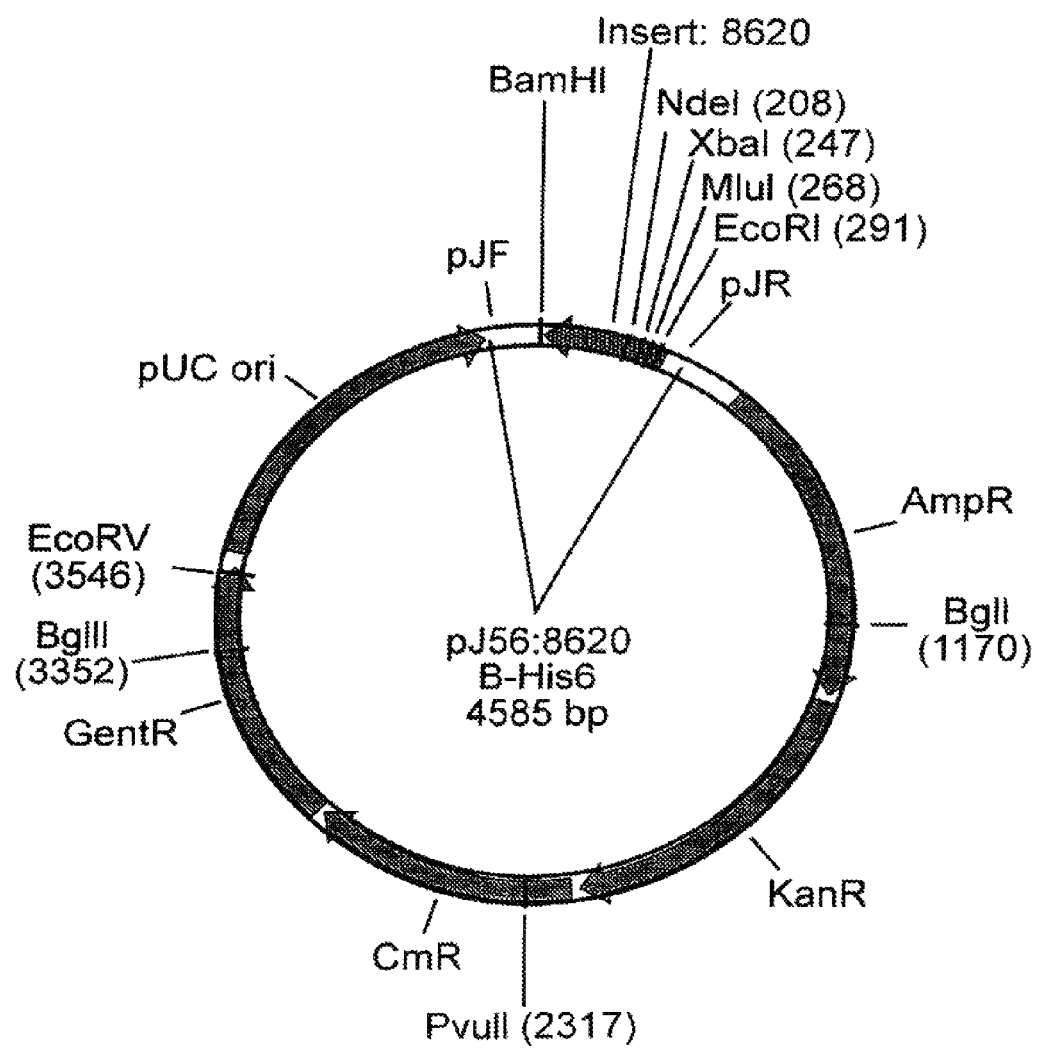
FIG. 5 depicts a schematic of the plasmid pJ56:8620.

A gene encoding the "B domain" of protein A is synthesized by standard method using a DNA synthesizer. The 5' end of the gene includes a codon for an initiating methionine as well as six histidine codons at the 3' end of the gene. The gene is provided in vector pJ56:8620. The parent vector pJ56 confers resistance to ampicillin, kanamycin, chloramphenicol and gentamicin. Appropriate restriction enzyme sites for the subsequent cloning of the gene into expression vectors are introduced into the gene at both 5' and 3' ends. A plasmid map of the vector is shown in FIG. 5.

Glycine at position 29 is mutated to each of the 19 other amino acids by PCR-based methods using the Phusion High-Fidelity DNA polymerase (New England Biolabs, Ipswich, Mass.). Phosphorylated primers are purchased from IDT DNA (Coralville, Iowa), as 100 µM solution in Tris EDTA buffer. The mutagenic primer has the sequence: 5'(P)GAAGAACAACGCAACNNNTTCATTCAGA (SEQ ID NO:19) where NNN represents the three bases encoding the amino acid at position 29. The non-mutagenic primer has the sequence 5'(P)GTTCAGGTTCGGCAGATGCAGGAT (SEQ ID NO:20). PCR is performed in 50 µL reactions containing dNTPs (0.2 mM each), 0.5 mM of each primer, 10 pg template plasmid, and 1 U of Phusion enzyme. PCR is carried out according to the scheme outlined in Table II.

TABLE II

| PCR conditions | | | |
|---|---|---|---|
| Cycle description | Temperature | Time | # of cycles |
| Initial denaturation | 98° C. | 30 seconds | 1 cycle |
| Denaturation | 98° C. | 30 seconds | 25 cycles |
| Annealing | 56° C. | 30 seconds | |
| Extension | 72° C. | 2 minutes | |
| Final extension | 98° C. | 10 minutes | 1 cycle |
| | 4° C. | Hold | |

PCR reactions are treated with the restriction enzyme DpnI (New England Biolabs, Ipswich, Mass.) to reduce wild type background. To each 50 μL PCR reaction, about 1 μL of DpnI enzyme is added and the samples are incubated for about one hour at 37° C.

E. coli NEB5α competent cells (New England Biolabs, Ipswich, Mass.) are transformed with 2 μL of the DpnI-treated PCR reaction. Cells are thawed on ice, and 2 μL of the PCR reaction is added to 25 μL of cells. Following about a 30-minute incubation on ice, cells are heat shocked for 30 seconds at about 42° C. Cells are allowed to recover for about 5 minutes on ice, and then 125 μL of SOC media (New England BioLabs) is added. Cells are incubated for about one hour at 37° C., and then 100 μL are plated on LB plates (Northeast Laboratory Services, Winslow, Me.) containing 100 μg/mL ampicillin and grown overnight at about 37° C. In order to obtain purified DNA, individual colonies are picked for overnight culture in LB containing 100 μg/mL ampicillin. DNA is purified using spin mini-prep kits from Qiagen (Valencia, Calif.). Primer pJR (5' GAATATGGCT-CATAACACCCCTTG) (SEQ ID NO:21) is used for sequencing the mini-prepped DNA to confirm the identity of each clone (MWG Biotech, Huntsville Ala.).

Following sequence confirmation of the various clones, the gene for each SpA variant is subcloned into a plasmid for expression of the variant in bacterial cells. Plasmid is digested with the appropriate restriction enzymes (New England Biolabs, Ipswich, Mass.), and the insert is gel purified on 1% agarose Reliant FastLane gels (Lonza Inc., Allendale, N.J.). The relevant band is cut out of the gel and purified using the gel extraction kit from Qiagen (Valencia, Calif.). The purified insert is ligated into the backbone of a suitable expression vector using T4 DNA ligase (New England Biolabs, Ipswich, Mass.). The resulting plasmid is used to transform E. coli NEB5α competent cells as described above.

Example 2

Expression and Purification of Protein A Variants

Any suitable bacterial expression system can be used for expressing the various SpA variants. For example, the protein may be expressed in Escherichia coli such as strain BL21(DE3) (Promega, Madison Wis.) from a pET vector such as pET11a (Novagen, Madison Wis.). A single colony is picked from a plate and grown overnight at about 37° C. in LB media containing 100 μg/mL ampicillin. The overnight culture is diluted 100-fold into fresh LB media containing 100 μg/mL ampicillin and grown to a cell density such that the optical density at 600 nm is ~0.8. Following the addition of 1 mM isopropyl-beta-D-thiogalactopyranoside, cells are grown for an additional two hours. Expression is confirmed by SDS-PAGE analysis and Western blotting. An exemplary protein A western blot is shown in FIG. 8, which shows that protein A expression from vector PET11a:8620 in E. coli BL21 (DE3) cells is detected using a chicken IgY anti-protein A antibody.

Cells are harvested by centrifugation (4000 rpm, 4° C., 5 minutes) and resuspended in 3 mL of phosphate buffered saline containing 20 mM imidazole. Cells are lysed by sonication, and cell debris is pelleted by centrifugation (4000 rpm, 4° C., 30 minutes). SpA variants are purified using NiNTA spin columns (Qiagen), applying 400 μL cell lysate per spin column. Columns are washed with 2×600 μL phosphate buffered saline containing 20 mM imidazole, and SpA is eluted in 2×200 μL phosphate buffered saline containing 200 mM imidazole. SpA is dialyzed overnight into PBS. Protein concentration is confirmed using the Dc protein assay (Bio-Rad Laboratories, Hercules, Calif.) relative to a standard curve prepared with bovine serum albumin.

Example 3

Binding of SpA Variants to Fc and Fab Fragments

Each SpA variant is subsequently tested for the ability to bind Fc and Fab using NiNTA agarose resin (Qiagen). Fc and F(ab)$_2$ fragments are obtained from Jackson ImmunoResearch (West Grove, Pa.). Each SpA variant is diluted to a concentration of 0.11 mg/mL, Fc is diluted to a concentration of 0.44 mg/mL and F(ab)$_2$ is diluted to a concentration of 0.92 mg/mL, in phosphate buffered saline containing 20 mM imidazole. The NiNTA agarose resin is resuspended and about 20 μl of the resin slurry is pipetted into a 0.5 ml microfuge tube. The resin is subsequently pelleted and the supernatant is discarded. The resin is washed with about 100 μl PBS with 20 mM imidazole, incubated at room temperature for about 15 mins and pelleted again. The supernatant is discarded. About 250 μl of each SpA variant at 0.11 mg/ml or PBS control is loaded onto the resin column in duplicates and incubated for about 30 mins at room temperature. The resin is pelleted and the supernatant is saved for analysis. The pellet is washed three times with 100 μl of PBS plus 20 mM imidazole each time, incubated for 5 mins and pelleted again. The supernatant is discarded. About 100 μl of Fc or F(ab)$_2$ is tested for binding with each of the SpA variants or the PBS control by incubating with the resin for about 30 mins. The resin is subsequently pelleted and the supernatant is saved for analysis. The resin is washed again three times with about 100 μl of PBS plus 20 mM imidazole each time, incubated for 5 mins and pelleted. The supernatant is discarded this time. The bound fraction is eluted with about 100 μl of PBS plus 20 mM imidazole, incubated for about 15 mins and pelleted. The supernatant is saved for further analysis. The samples are subsequently analyzed by SDS-PAGE on 4-15% gradient gels purchased from Bio-Rad Laboratories, CA, as depicted in FIGS. 9-12.

The binding of five protein A variants to Fc and F(ab)2 is tested by surface plasmon resonance biosensor analysis. All experiments are carried out in phosphate buffered saline (PBS) containing 0.005% Tween-20. Protein A variants are immobilized on ProteOn GLC sensor chip (Bio-Rad Laboratories, Hercules, Calif.) via amine chemistry, with coupling to a level of 500 RU. Three fold-dilution series of Fc and F(ab)$_2$ fragments (Jackson ImmunoResearch Laboratories, West Grove, Pa.) are prepared, with protein concentrations ranging from 45 nM to 185 pM, and each concentration is analyzed in duplicate. Each concentration of Fc or F(ab)$_2$ is injected for 250 seconds, followed by 3.5 hours of PBS to measure dissociation rates. Data are fit to a heterogeneous two-site model in order to obtain on- and off-rates and ($k_{on}$ and $k_{off}$). As depicted in FIGS. 13A-13E, the wild type glycine 29 protein, and each of G29A, G29R, G29K and G29L bind Fc. FIGS. 14A-14E show that the wild type G29 is observed to bind Fab, and G29A shows weak but detectable F(ab)2 binding. No F(ab)2 binding is seen for G29R, G29K or G29L.

Fc and Fab binding are also evaluated following immobilization of the SpA variants on chromatography resins. Controlled pore glass beads (50 mL each, mean particle size of 60 µm, mean pore diameter of 800 Å) are functionalized with Protein A or Protein A variant according to the method for coupling Protein A to a solid support described in International PCT Application No. WO 90/09237, the entire contents of which are incorporated by reference herein. After ligand coupling, the samples are washed three times with 150 mL volume of each (in order): 0.1M Tris with 0.15M NaCl, pH 8 followed by 0.05M Acetic Acid. Afterwards, the samples are equilibrated and stored in PBS with azide.

Controlled pore glass affinity resins immobilized with the corresponding ligand are packed in a 6.6 mm id×70 mm L OmniFit columns. Buffers used in the experiment are: (A) 5 mM sodium phosphate buffer, pH 7.2; and (B) 50 mM sodium phosphate, pH 2, and the flow rate is 1.2 mL/min. After the column is equilibrated in the starting buffer A, 100 µL of F(ab)2 or Fc at 1~2 mg/mL (Jackson ImmunoResearch, West Grove, Pa.) in buffer A is injected into the column. After 10 column volume (CV) of buffer A, buffer B is mixed in over 20 CV in a linear gradient. Ten more column volumes of Buffer B run through the column before the column was regenerated by 2 CV of 6 M guanidine hydrochloride. As depicted in FIGS. 15A and 15B, the wild type glycine 29 protein as well as each of G29A, G29R, G29K and G29L bind Fc. The wild type G29 is observed to bind Fab, and G29A shows weak but detectable F(ab)2 binding. No F(ab)2 binding is seen for G29R, G29K or G29L.

In another exemplary experiment, a full set of protein A variants are tested for Fc and Fab binding by capturing them on NiNTA agarose resin (Qiagen). Briefly, His-tagged protein A variants having an amino acid substitution at position 29 of the wtSpA are added in excess to the resin, the resin is washed with PBS containing 20 mM imidazole followed by the addition of Fc or Fab portion of an immunoglobulin. The resin is washed again with PBS containing 20 mM imidazole followed by elution of SpA and IgG fragments with PBS containing 200 mM imidazole. The resulting elution fractions are analysed on a 4-20% gradient gel (BioRad) followed by Commassie blue staining (Pierce). Resin with no protein A is used as a negative control. The results of an exemplary experiment are summarized below in Table III. While no apparent difference in Fc binding is observed among the different variants, the Fab binding is markedly reduced for most of the variants. Most of the variants exhibit Fab binding that is less than 15% compared to wild type. Residual Fab binding of 24% or greater is observed for three of the variants (G29A, G29T, and G29W).

TABLE III

| Variant | Fab binding quantitated by densitometry (percentage of wild type glycine) |
|---------|------------------------------------------------------------------------|
| WT | 100 |
| G29K | 4 |
| G29R | 9 |
| G29L | 7 |
| G29A | 24 |

TABLE III-continued

| Variant | Fab binding quantitated by densitometry (percentage of wild type glycine) |
|---------|------------------------------------------------------------------------|
| G29C | 5 |
| G29D | 8 |
| G29E | 11 |
| G29F | 7 |
| G29H | 5 |
| G29I | 8 |
| G29M | 9 |
| G29N | 8 |
| G29P | 14 |
| G29Q | 11 |
| G29S | 8 |
| G29T | 37 |
| G29V | 10 |
| G29W | 66 |
| G29Y | 11 |
| control | 11 |

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about," Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

References:

Fab binding: Melissa A. Starovasnik, Mark P. O'connell, Wayne J. Fairbrother, And Robert F. Kelley (1999). Antibody variable region binding by *Staphylococcal* protein A: Thermodynamic analysis and location of the Fv binding site on E-domain. *Protein Science* 8, 1423-1431.

Fc binding constant: Susanne Gülich, Mathias Uhlén, Sophia Hober (2000) Protein engineering of an IgG-binding domain allows milder elution conditions during affinity chromatography. *Journal of Biotechnology* 76, 233-244

What is claimed is:

1. A method of affinity purifying one or more immunoglobulins from a sample, the method comprising the steps of:

(a) providing a sample comprising one or more immunoglobulins;

contacting the sample with a chromatography matrix under conditions such that the one or more immunoglobulins bind to the matrix, wherein the chromatography matrix comprises an immunoglobulin-binding protein which binds an Fc portion of the one or more immunoglobulins but exhibits reduced binding to a Fab portion of the one or more immunoglobulins relative to wild-type protein A and comprises one or more isolated domains comprising the amino acid sequence set forth in SEQ ID NO:10, SEQ ID NO:11 or SEQ ID NO:12, and wherein the one or more isolated domains comprise: (i) at least the glycine residue at position 29 of SEQ ID NO: 10 replaced with an amino acid residue selected from the group consisting of a lysine residue, a leucine residue and an arginine residue, as shown in SEQ ID NO: 23, SEQ ID NO: 24 and SEQ ID NO: 25, respectively; or (ii) at least the glycine residue at position 29 of SEQ ID NO: 11 replaced with an amino acid residue selected from the group consisting of a lysine residue, a leucine residue and an arginine residue, as shown in SEQ ID NO:26, SEQ ID NO: 27 and SEQ ID NO: 28, respectively; or (iii) at least the alanine at position 29 of SEQ ID NO:12 replaced with an amino acid residue selected from the group consisting of a lysine residue, a leucine residue and an arginine residue, as shown in SEQ ID NO: 29, SEQ ID NO: 30 and SEQ ID NO: 31, respectively, and (b) recovering the one or more bound immunoglobulins by eluting under suitable conditions.

2. The method of claim 1, wherein the one or more immunoglobulins is selected from the group consisting of IgG, IgA or IgM, or a fragment thereof.

3. The method of claim 1, wherein the one or more immunoglobulins is an IgG or a fragment thereof.

4. The method of claim 1, wherein the Fc portion of an immunoglobulin is part of an Fc fusion protein.

5. The method of claim 1, wherein the amino acid residue is lysine.

6. The method of claim 1, wherein the immunoglobulin-binding protein is coupled to a solid support.

7. The method of claim 6, wherein the solid support is selected from the group consisting of controlled pore glass, agarose, methacrylate, and polystyrene.

8. The method of claim 1, wherein the immunoglobulin-binding protein further comprising at least a portion of the carboxy-terminal region of *Staphylococcus* protein A.

* * * * *